(12) United States Patent
Lu et al.

(10) Patent No.: US 12,186,570 B2
(45) Date of Patent: *Jan. 7, 2025

(54) BRANCHED PROXIMAL CONNECTORS FOR HIGH DENSITY NEURAL INTERFACES

(71) Applicant: Verily Life Sciences LLC, South San Francisco, CA (US)

(72) Inventors: Bo Lu, South San Francisco, CA (US); Kedar Shah, San Francisco, CA (US)

(73) Assignee: Verily Life Sciences LLC, Dallas, TX (US)

(*) Notice: Subject to any disclaimer, the term of this patent is extended or adjusted under 35 U.S.C. 154(b) by 211 days.

This patent is subject to a terminal disclaimer.

(21) Appl. No.: 17/847,457

(22) Filed: Jun. 23, 2022

(65) Prior Publication Data

US 2022/0323773 A1    Oct. 13, 2022

Related U.S. Application Data

(63) Continuation of application No. 16/658,596, filed on Oct. 21, 2019, now Pat. No. 11,395,923.

(Continued)

(51) Int. Cl.
  *A61N 1/375* (2006.01)
  *A61N 1/05* (2006.01)
  (Continued)

(52) U.S. Cl.
  CPC ......... *A61N 1/3754* (2013.01); *A61N 1/0551* (2013.01); *H01L 24/46* (2013.01);
  (Continued)

(58) Field of Classification Search
  CPC .... H05K 1/0271; H05K 1/0393; H05K 1/092; H05K 1/115; H05K 1/118;
  (Continued)

(56) References Cited

U.S. PATENT DOCUMENTS

| 5,324,322 A | 6/1994 | Grill, Jr. et al. |
| 6,210,339 B1 | 4/2001 | Kiepen et al. |

(Continued)

FOREIGN PATENT DOCUMENTS

| CN | 1820799 A | 8/2006 |
| CN | 102543104 A | 7/2012 |

(Continued)

OTHER PUBLICATIONS

U.S. Appl. No. 17/276,439, Non-Final Office Action, Mailed On Jan. 29, 2024, 22 pages.

(Continued)

*Primary Examiner* — George Manuel
(74) *Attorney, Agent, or Firm* — Kilpatrick Townsend & Stockton LLP

(57) ABSTRACT

The present disclosure relates to branched proximal connectors for high density neural interfaces and methods of microfabricating the branched proximal connectors. Particularly, aspects of the present disclosure are directed to a branched connector that includes a main body having a base portion of a supporting structure and a plurality of conductive traces formed on the base portion, and a plurality of plugs extending from the main body. Each plug of the plurality of plugs include an end portion of the supporting structure comprised of the one or more layers of dielectric material, and a subset of conductive traces from the plurality of conductive traces. Each trace from the subset of conductive traces terminates at a bond pad exposed on a surface of the end portion of the supporting structure.

20 Claims, 27 Drawing Sheets

Related U.S. Application Data

(60) Provisional application No. 62/768,562, filed on Nov. 16, 2018.

(51) Int. Cl.
*H01L 23/00* (2006.01)
*H05K 1/09* (2006.01)
*H05K 1/11* (2006.01)

(52) U.S. Cl.
CPC .............. *H05K 1/092* (2013.01); *H05K 1/115* (2013.01); *H01R 2201/12* (2013.01)

(58) Field of Classification Search
CPC ... H05K 2201/0125; H05K 2201/0129; H05K 2201/0141; H05K 2201/0145; H05K 2201/0154; H05K 2201/052; H05K 2201/068; H05K 2201/09254; H05K 2201/10151; H01R 2201/12; H01L 24/46; A61N 1/0534; A61N 1/0551; A61N 1/3752; A61N 1/3754; A61N 1/00; A61N 2/00; A61N 5/00; A61N 7/00

See application file for complete search history.

(56) References Cited

U.S. PATENT DOCUMENTS

| | | | |
|---|---|---|---|
| 6,662,035 | B2 | 12/2003 | Sochor |
| 8,380,325 | B2 | 2/2013 | McDonald |
| 9,829,028 | B2 | 11/2017 | Changsrivong et al. |
| 11,395,923 | B2 | 7/2022 | Lu et al. |
| 12,070,611 | B2 | 8/2024 | Sabesan et al. |
| 12,106,876 | B2 | 10/2024 | Karicherla et al. |
| 2003/0135253 | A1 | 7/2003 | Kokones et al. |
| 2005/0137665 | A1 | 6/2005 | Cole |
| 2007/0261115 | A1 | 11/2007 | Gerber et al. |
| 2008/0096310 | A1 | 4/2008 | Modi et al. |
| 2008/0147158 | A1 | 6/2008 | Zweber et al. |
| 2009/0259265 | A1* | 10/2009 | Stevenson .......... A61N 1/37512 607/2 |
| 2010/0065963 | A1 | 3/2010 | Eldridge et al. |
| 2011/0072659 | A1 | 3/2011 | Swanson et al. |
| 2011/0077699 | A1 | 3/2011 | Swanson et al. |
| 2011/0301665 | A1 | 12/2011 | Mercanzini et al. |
| 2012/0071870 | A1 | 3/2012 | Salahieh et al. |
| 2013/0282090 | A1 | 10/2013 | Decre et al. |
| 2014/0324117 | A1 | 10/2014 | Bedenbaugh |
| 2015/0157862 | A1 | 6/2015 | Greenberg et al. |
| 2015/0165191 | A1 | 6/2015 | Frericks |
| 2015/0273181 | A1 | 10/2015 | Leeflang |
| 2016/0128588 | A1 | 5/2016 | Melosh et al. |
| 2016/0144078 | A1 | 5/2016 | Young et al. |
| 2016/0144165 | A1 | 5/2016 | Young et al. |
| 2016/0144166 | A1 | 5/2016 | Decré al. |
| 2016/0144168 | A1 | 5/2016 | Tol et al. |
| 2016/0144185 | A1 | 5/2016 | Young et al. |
| 2016/0351292 | A1 | 12/2016 | Toth et al. |
| 2017/0065813 | A1 | 3/2017 | Chen |
| 2017/0319846 | A1 | 11/2017 | Plachta et al. |
| 2018/0117312 | A1 | 5/2018 | Schmidt et al. |
| 2018/0169406 | A1 | 6/2018 | Shah et al. |
| 2018/0229041 | A1 | 8/2018 | Pepin et al. |
| 2018/0303595 | A1* | 10/2018 | Opie .................... A61F 2/90 |
| 2018/0345009 | A1 | 12/2018 | Shah |

FOREIGN PATENT DOCUMENTS

| | | |
|---|---|---|
| CN | 102683228 A | 9/2012 |
| CN | 103608067 A | 2/2014 |
| CN | 104766850 A | 7/2015 |
| CN | 105169554 A | 12/2015 |
| CN | 105392522 A | 3/2016 |
| CN | 105517623 A | 4/2016 |
| CN | 105727444 A | 7/2016 |
| CN | 106573141 A | 4/2017 |
| CN | 107297023 A | 10/2017 |
| WO | 2010055453 A1 | 5/2010 |
| WO | 2016201151 A1 | 12/2016 |

OTHER PUBLICATIONS

U.S. Appl. No. 17/276,439, Notice of Allowance, Mailed On Apr. 24, 2024, 14 pages.
U.S. Appl. No. 17/277,000, "Notice of Allowability", Mar. 22, 2024, 5 pages.
Application No. CN201980061342.5, Office Action, Mailed On Jan. 26, 2024, 11 pages.
Application No. EP19778771.6, Office Action, Mailed On Feb. 16, 2024, 6 pages.
EP19883619.9, "Intention to Grant", Feb. 23, 2024, 9 pages.
Malesevic et al., "A Multi-pad Electrode Based Functional Electrical Stimulation System for Restoration of Grasp", Journal of Neuro Engineering and Rehabilitation, vol. 9, No. 66, Sep. 25, 2012, pp. 1-12.
Europe Patent Application No. 19778771.6, Communication pursuant to Article 94(3) EPC, dated Feb. 27, 2023.
U.S. Appl. No. 17/276,439, Office Action, dated May 10, 2023.
U.S. Appl. No. 17/276,439, Final Office Action, Mailed On Oct. 25, 2023, 20 pages.
U.S. Appl. No. 17/277,000, Final Office Action, Mailed On Oct. 13, 2023, 9 pages.
U.S. Appl. No. 17/277,000, Notice of Allowance, Mailed On Jan. 3, 2024, 7 pages.
U.S. Appl. No. 17/277,000, Non-Final Office Action, Mailed On Jul. 20, 2023, 7 pages.
Application No. EP19778771.6, Office Action, Mailed On Jul. 10, 2023, 6 pages.
"Bal Contact® Electrical Contacts", Bal Seal Engineering, Available Online at https://www.balseal.com/contact/, Oct. 16, 2019, pp. 1-2.
U.S. Appl. No. 16/658,596, Notice of Allowance, Mailed On Mar. 25, 2022, 8 pages.
Application No. PCT/US2019/051165, International Preliminary Report on Patentability, Mailed On Apr. 1, 2021, 9 pages.
Application No. PCT/US2019/051165, International Search Report and Written Opinion, Mailed On Feb. 4, 2020, 14 pages.
PCT/US2019/051165, "Invitation to Pay Additional Fees and, Where Applicable, Protest Fee", Dec. 10, 2019, 10 pages.
Application No. PCT/US2019/051168, International Preliminary Report on Patentability, Mailed On Apr. 1, 2021, 11 pages.
Application No. PCT/US2019/051168, International Search Report and Written Opinion, Mailed On Dec. 18, 2019, 17 pages.
Application No. PCT/US2019/057178, International Preliminary Report on Patentability, Mailed On May 27, 2021, 7 pages.
Application No. PCT/US2019/057178, International Search Report and Written Opinion, Mailed On Jan. 23, 2020, 9 pages.
Application No. EP19883619.9, Extended European Search Report, Mailed On Jul. 6, 2022, 8 pages.
Application No. CN201980061342.5, Notice of Decision to Grant, Mailed On Jul. 24, 2024, 7 pages with English summary.
Application No. CN201980075566.1, Office Action, Mailed On Jul. 2, 2024, 13 pages with English translation.

\* cited by examiner

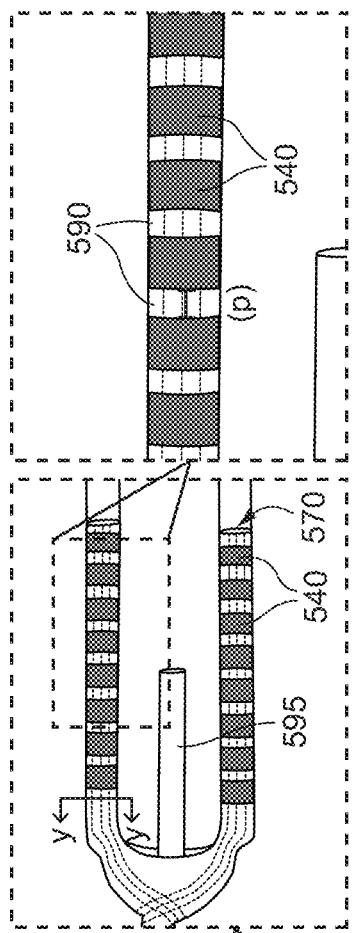
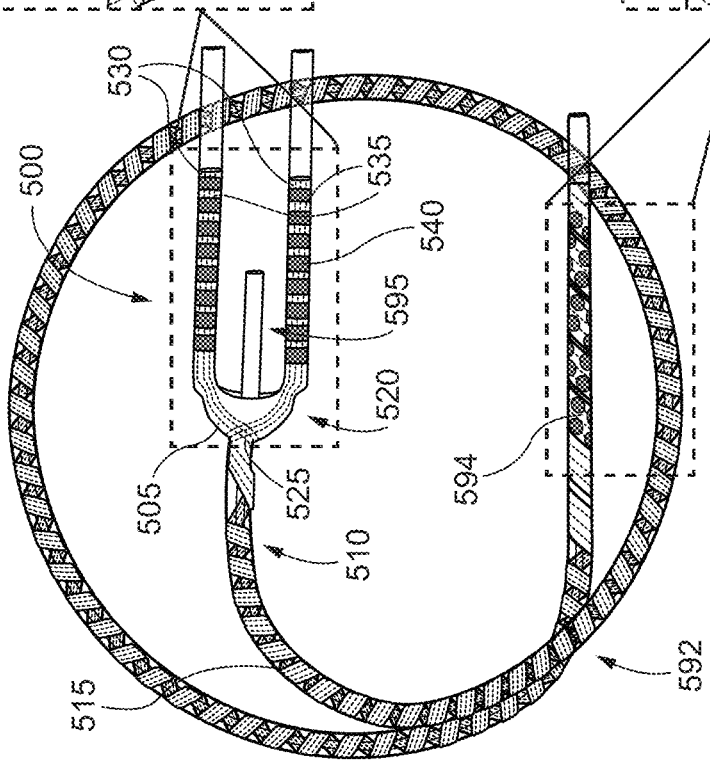
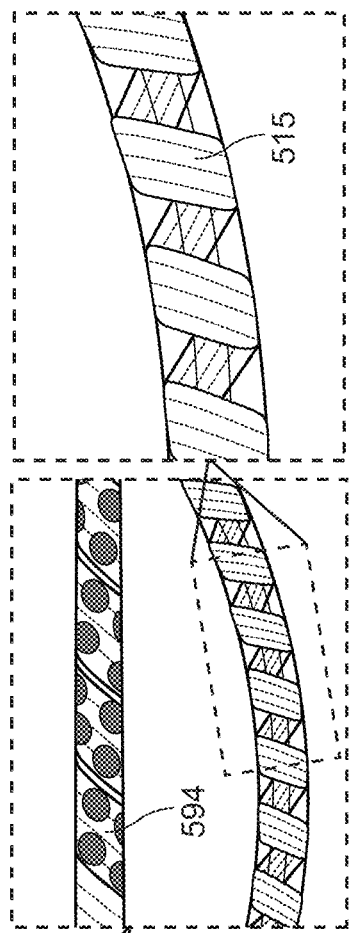
FIG. 5A
FIG. 5B
FIG. 5C
FIG. 5D
FIG. 5E y-y

BRANCHED PROXIMAL CONNECTORS FOR HIGH DENSITY NEURAL INTERFACES

CROSS-REFERENCE TO RELATED APPLICATIONS

The present application is a continuation of U.S. application Ser. No. 16/658,596, filed Oct. 21, 2019, which claims the benefit of priority to U.S. Provisional Application No. 62/768,562, filed Nov. 16, 2018, the entire contents of which are incorporated by reference herein for all purposes.

FIELD

The present disclosure relates to implantable neuromodulation devices and methods of fabrication, and in particular to branched proximal connectors for high density neural interfaces and methods of microfabricating the branched proximal connectors.

BACKGROUND

Normal neural activity is an intricate balance of electrical and chemical signals, which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems that deliver electrical, chemical or other agents to reversibly modify brain and nerve cell activity. The most common neuromodulation therapy is spinal cord stimulation to treat chronic neuropathic pain. In addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis; gastric and colonic stimulation for gastrointestinal disorders such as dysmotility or obesity; vagus nerve stimulation for epilepsy, obesity or depression; carotid artery stimulation for hypertension, and spinal cord stimulation for ischemic disorders such as angina and peripheral vascular disease.

Neuromodulation devices and systems tend to have a similar form factor, derived from their predecessors, e.g. the pacemaker or defibrillator. Such neuromodulation devices and systems typically consist of an implant comprising a neurostimulator having electronics connected to a lead assembly that delivers electrical pulses to electrodes interfaced with nerves or nerve bundles via an electrode assembly. The lead assembly is typically formed of a conductive material and takes the form of an insulated wire (e.g., a dedicated channel) connected to the electrodes via a first connector on one end (e.g., a distal end) and the electronics of the neurostimulator via a second connector on another end (e.g., a proximal end). In some instances (e.g., deep implants), the lead assembly comprises additional conductors and connectors such as extension wires or a cable connected via connectors between the electrodes and the electronics of the neurostimulator.

Conventional neuromodulation devices include between four and sixteen electrodes, and thus typically include four to sixteen channels or wires connected respectively to the electrodes at the distal end and the electronics of the neurostimulator at the proximal end. However, there is a need for high density neural interfaces that include greater than sixteen electrodes to interface with larger tissue volumes, to recruit smaller populations of neurons for recording, or to provide more targeted therapy by tailoring the electrical stimulation parameters and activated tissue volume. Increasing the density or number of electrodes can increase the number of channels or wires needed to connect the electrodes and the electronics of the neurostimulator. In order to implement high channel or wire counts, there is a need for reliable electrical connections that can maintain contact and electrical isolation in a subject body (e.g., a patient body) for many years. Typically, a lead assembly containing a high channel or wire count needs to be permanently connected to the electronics. However, this is not ideal because the electronics need to be replaced every few years to upgrade them or to replace batteries, and surgeons have a strong preference not to remove the lead assembly from the neural tissue due to the risk to the patient. Therefore, there is a need for reliable and non-permanent connectors for lead assemblies having high density neural interfaces.

BRIEF SUMMARY

In various embodiments, a branched connector is provided that comprises: a main body comprising a base portion of a supporting structure and a plurality of conductive traces formed on the base portion, where the base portion of the supporting structure is comprised of one or more layers of dielectric material; and a plurality of plugs extending from the main body. Each plug of the plurality of plugs comprises: an end portion of the supporting structure comprised of the one or more layers of dielectric material; and a subset of conductive traces from the plurality of conductive traces, where each trace from the subset of conductive traces terminates at a bond pad exposed on a surface of the end portion of the supporting structure.

In some embodiments, the dielectric material is polyimide, liquid crystal polymer, parylene, polyether ether ketone, or a combination thereof. In some embodiments, the plurality of conductive traces are comprised of one or more layers of conductive material, and the conductive material is platinum (Pt), platinum/iridium (Pt/Ir), titanium (Ti), gold/titanium (Au/Ti), or any alloy thereof.

In some embodiments, a coefficient of thermal expansion for the plurality of conductive traces is approximately equal to a coefficient of thermal expansion for the supporting structure.

In some embodiments, the base portion of the supporting structure and each of the end portions of the supporting structure are monolithic. Optionally, each of the end portions of the supporting structure are planar. Optionally, each of the end portions of the supporting structure are a cylindrical tube.

In some embodiments, the one or more layers of dielectric material comprise a first layer of dielectric material and a second layer of dielectric material with the subset of conductive traces buried between the first layer of dielectric material and the second layer of dielectric material.

In some embodiments, each bond pad is a split annular ring positioned around an axis of the cylindrical tube and exposed on the surface of the cylindrical tube. Optionally, each split annular ring is spaced apart from one another on the surface of the cylindrical tube by a region of the first layer of the dielectric material. Optionally, a width of the region of the first layer of the dielectric material that separates each split annular ring is between 1.0 mm to 10 mm.

In some embodiments, the cylindrical tube comprises: (i) the one or more layers of dielectric material, wherein the first layer of dielectric material defines an outer diameter of the cylindrical tube and the second layer of dielectric material defines an inner diameter of the tube; and (ii) a core that at least partially fills an interior of the cylindrical tube defined by the inner diameter of the cylindrical tube. Optionally, the one or more layers of dielectric material are at least partially wrapped around the core. Optionally, the one or more layers of dielectric material are formed as a split cylindrical tube wrapped around the core, and the split cylindrical tube comprises a gap for the split having a predefined width. Optionally, the predefined width is between 0.1 mm and 10 mm.

In some embodiments, the first layer of dielectric material comprises at least one via for each bond pad, and the via comprises a conductive material for electrically connecting each bond pad to at least one trace of the subset of conductive traces such that each trace from the subset of conductive traces terminates at a bond pad.

In some embodiments, the first layer of dielectric material is a high temperature liquid crystal polymer, and the second layer of dielectric material is a low temperature liquid crystal polymer.

In some embodiments, the core is comprised of one or more layers of material such that the core has a Shore durometer of greater than 70D. Optionally, the one or more layers of material of the core is polyimide, liquid crystal polymer, parylene, polyether ether ketone, polyurethane, metal, or a combination thereof. Optionally, the one or more layers of material of the core is thermosetting or thermoplastic polyurethane.

In various embodiments, a monolithic thin-film lead assembly is provided that comprises: a cable comprising a proximal end, a distal end, a supporting structure that extends from the proximal end to the distal end, and a plurality of conductive traces formed on a portion of the supporting structure, where the supporting structure is comprised of one or more layers of dielectric material; an electrode assembly formed on the supporting structure at the distal end of the cable, where the electrode assembly comprises one or more electrodes in electrical connection with one or more conductive traces of the plurality of conductive traces; and a branched connector formed on the supporting structure at the proximal end of the cable, where the branched connector comprises: (i) a main body comprising the supporting structure and the plurality of conductive traces, and (ii) a plurality of plugs extending from the main body, each plug of the plurality of plugs comprises the supporting structure and a subset of conductive traces from the plurality of conductive traces, wherein each trace from the subset of conductive traces terminates at a bond pad exposed on a surface of the supporting structure.

In some embodiments, the dielectric material is polyimide, liquid crystal polymer, parylene, polyether ether ketone, or a combination thereof. In some embodiments, the plurality of conductive traces are comprised of one or more layers of conductive material, and the conductive material is platinum (Pt), platinum/iridium (Pt/Ir), titanium (Ti), gold/titanium (Au/Ti), or any alloy thereof. Optionally, the supporting structure of each plug is planar. Optionally, the supporting structure of each plug is a cylindrical tube.

In some embodiments, the supporting structure of each of the plugs comprises a first layer of dielectric material and a second layer of dielectric material with the subset of conductive traces buried between the first layer of dielectric material and the second layer of dielectric material. In some embodiments, each bond pad is a split annular ring positioned around an axis of the cylindrical tube and exposed on the surface of the cylindrical tube. Optionally, each split annular ring is spaced apart from one another on the surface of the cylindrical tube by a region of the first layer of the dielectric material.

In some embodiments, the cylindrical tube comprises: (i) the one or more layers of dielectric material, wherein the first layer of dielectric material defines an outer diameter of the cylindrical tube and the second layer of dielectric material defines an inner diameter of the tube; and (ii) a core that at least partially fills an interior of the cylindrical tube defined by the inner diameter of the cylindrical tube. Optionally, the one or more layers of dielectric material are at least partially wrapped around the core.

In some embodiments, the one or more layers of dielectric material are formed as a split cylindrical tube wrapped around the core, and the split cylindrical tube comprises a gap for the split having a predefined width.

In some embodiments, the first layer of dielectric material comprises at least one via for each bond pad, and the via comprises a conductive material for electrically connecting each bond pad to at least one trace of the subset of conductive traces such that each trace from the subset of conductive traces terminates at a bond pad. In some embodiments, the first layer of dielectric material is a high temperature liquid crystal polymer, and the second layer of dielectric material is a low temperature liquid crystal polymer. Optionally, the core is comprised of one or more layers of material such that the core has a Shore durometer of greater than 70D.

In various embodiments, a thin-film lead assembly is provided that comprises: a cable comprising a proximal end, a distal end, a first supporting structure that extends from the proximal end to the distal end, and a plurality of conductive traces formed on a portion of the first supporting structure; an electrode assembly formed on the first supporting structure at the distal end of the cable, wherein the electrode assembly comprises one or more electrodes in electrical connection with one or more conductive traces of the plurality of conductive traces; and a branched connector comprising: (i) a main body comprising a second supporting structure and a plurality of conductive connector traces, and (ii) a plurality of plugs extending from the main body, each plug of the plurality of plugs comprises the second supporting structure and a subset of conductive connecting traces from the plurality of conductive connecting traces, where each trace from the subset of conductive connecting traces terminates at a bond pad exposed on a surface of the second supporting structure, and where the plurality of conductive connector traces of the branched connector are in electrical contact with the plurality of conductive traces of the cable, respectively.

In some embodiments, the second supporting structure is comprised of one or more layers of dielectric material, and the dielectric material is polyimide, liquid crystal polymer, parylene, polyether ether ketone, or a combination thereof. In some embodiments, the plurality of conductive connector traces are comprised of one or more layers of conductive material, and the conductive material is platinum (Pt), platinum/iridium (Pt/Ir), titanium (Ti), gold/titanium (Au/

Ti), or any alloy thereof. Optionally, the second supporting structure of each plug is planar. Optionally, the second supporting structure of each plug is a cylindrical tube.

In some embodiments, the second supporting structure of each of the plugs comprises a first layer of dielectric material and a second layer of dielectric material with the subset of conductive connecting traces buried between the first layer of dielectric material and the second layer of dielectric material. In some embodiments, each bond pad is a split annular ring positioned around an axis of the cylindrical tube and exposed on the surface of the cylindrical tube. Optionally, each split annular ring is spaced apart from one another on the surface of the cylindrical tube by a region of the first layer of the dielectric material.

In some embodiments, the cylindrical tube comprises: (i) the one or more layers of dielectric material, wherein the first layer of dielectric material defines an outer diameter of the cylindrical tube and the second layer of dielectric material defines an inner diameter of the tube; and (ii) a core that at least partially fills an interior of the cylindrical tube defined by the inner diameter of the cylindrical tube.

In some embodiments, the one or more layers of dielectric material are at least partially wrapped around the core. Optionally, the one or more layers of dielectric material are formed as a split cylindrical tube wrapped around the core, and the split cylindrical tube comprises a gap for the split having a predefined width. Optionally, the first layer of dielectric material comprises at least one via for each bond pad, and the via comprises a conductive material for electrically connecting each bond pad to at least one trace of the subset of conductive connecting traces such that each trace from the subset of conductive connecting traces terminates at a bond pad.

In some embodiments, the first layer of dielectric material is a high temperature liquid crystal polymer, and the second layer of dielectric material is a low temperature liquid crystal polymer. Optionally, the core is comprised of one or more layers of material such that the core has a Shore durometer of greater than 70D.

In various embodiments, a neuromodulation system is provided that comprises: a neurostimulator comprising an electronics module; a cable comprising a supporting structure and a plurality of conductive traces formed on a portion of the supporting structure, where the supporting structure is comprised of one or more layers of dielectric material; an electrode assembly formed on the supporting structure, where the electrode assembly comprises one or more electrodes in electrical connection with one or more conductive traces of the plurality of conductive traces; and a branched connector formed on the supporting structure at the proximal end of the cable, where the branched connector comprises: (i) a main body comprising the supporting structure and the plurality of conductive traces, and (ii) a plurality of plugs extending from the main body, each plug of the plurality of plugs comprises the supporting structure and a subset of conductive traces from the plurality of conductive traces, where the branched connector electrically connects each subset of conductive traces from the plurality of conductive traces to the electronics module.

In some embodiments, each trace from the subset of conductive traces terminates at a bond pad exposed on a surface of the supporting structure. Optionally, the dielectric material is polyimide, liquid crystal polymer, parylene, polyether ether ketone, or a combination thereof. In some embodiments, the plurality of conductive traces are comprised of one or more layers of conductive material, and the conductive material is platinum (Pt), platinum/iridium (Pt/Ir), titanium (Ti), gold/titanium (Au/Ti), or any alloy thereof. Optionally, the supporting structure of each plug is planar. Optionally, the supporting structure of each plug is a cylindrical tube.

In some embodiments, the supporting structure of each of the plugs comprises a first layer of dielectric material and a second layer of dielectric material with the subset of conductive traces buried between the first layer of dielectric material and the second layer of dielectric material. Optionally, each bond pad is a split annular ring positioned around an axis of the cylindrical tube and exposed on the surface of the cylindrical tube. Optionally, each split annular ring is spaced apart from one another on the surface of the cylindrical tube by a region of the first layer of the dielectric material.

In some embodiments, the cylindrical tube comprises: (i) the one or more layers of dielectric material, wherein the first layer of dielectric material defines an outer diameter of the cylindrical tube and the second layer of dielectric material defines an inner diameter of the tube; and (ii) a core that at least partially fills an interior of the cylindrical tube defined by the inner diameter of the cylindrical tube. Optionally, the one or more layers of dielectric material are at least partially wrapped around the core.

In some embodiments, the one or more layers of dielectric material are formed as a split cylindrical tube wrapped around the core, and the split cylindrical tube comprises a gap for the split having a predefined width.

In some embodiments, the first layer of dielectric material comprises at least one via for each bond pad, and the via comprises a conductive material for electrically connecting each bond pad to at least one trace of the subset of conductive traces such that each trace from the subset of conductive traces terminates at a bond pad.

In some embodiments, the first layer of dielectric material is a high temperature liquid crystal polymer, and the second layer of dielectric material is a low temperature liquid crystal polymer. Optionally, the core is comprised of one or more layers of material such that the core has a Shore durometer of greater than 70D.

In various embodiments, a method of manufacturing a branched connector is provided that comprises: obtaining a flexible printed circuit board structure comprising: (i) a main body comprising a supporting structure and a plurality of conductive traces, and (ii) a plurality of plugs extending from the main body, each plug of the plurality of plugs comprises the supporting structure and a subset of conductive traces from the plurality of conductive traces, where each trace from the subset of conductive traces terminates at a bond pad exposed on a surface of the supporting structure, and wherein the supporting structure comprise a first polymer layer and a second polymer layer with the subset of conductive traces buried between the first polymer layer and the second polymer layer; wrapping each of the plurality of plugs at least partially around a mandrel, respectively, such that each of the plurality of plugs is in a shape of a cylindrical tube; placing a heat shrink tube over each of the plurality of plugs and the mandrels to form a first intermediate structure; heating the first intermediate structure to shrink each of the heat shrink tubes and form a second intermediate structure; removing the mandrels from the second intermediate structure such that each of the plurality of plugs is left with a lumen; injecting the lumens of the second intermediate structure with a polymer to form a third intermediate structure; heating the third intermediate structure to form the branched connector with a plurality of cylindrical plugs; and removing the heat shrink tubes from the branched connector with the plurality of cylindrical plugs. Each of the plurality of cylindrical plugs comprises the first polymer layer and the second polymer layer at least partially wrapped around a core made of the polymer.

In some embodiments, the first polymer layer is polyimide, liquid crystal polymer, parylene, polyether ether ketone, or a combination thereof. In some embodiments, the second polymer layer is polyimide, liquid crystal polymer, parylene, polyether ether ketone, or a combination thereof. In some embodiments, the plurality of conductive traces and the subset of conductive traces are comprised of one or more layers of conductive material, and the conductive material is platinum (Pt), platinum/iridium (Pt/Ir), titanium (Ti), gold/titanium (Au/Ti), or any alloy thereof.

In some embodiments, each of the end portions is partially wrapped around the mandrel or the polymer tube, respectively such that the plurality of cylindrical end portions are a plurality of split cylindrical end portions, and each split cylindrical end portion of the plurality of split cylindrical end portions comprises a gap for the split having a predefined width.

In some embodiments, the method further comprises forming a third polymer layer on the second polymer layer in a region between the main body portion and the plurality of end portions. In some embodiments, the third polymer layer is silicone.

In various embodiments, a method of manufacturing a branched connector is provided that comprises: obtaining a flexible printed circuit board structure comprising: (i) a main body comprising a supporting structure and a plurality of conductive traces, and (ii) a plurality of plugs extending from the main body, each plug of the plurality of plugs comprises the supporting structure and a subset of conductive traces from the plurality of conductive traces, where each trace from the subset of conductive traces terminates at a bond pad exposed on a surface of the supporting structure, and wherein the supporting structure comprise a first polymer layer and a second polymer layer with the subset of conductive traces buried between the first polymer layer and the second polymer layer; wrapping each of the plurality of plugs at least partially around a polymer tube, respectively, such that each of the plurality of plugs is in a shape of a cylindrical tube; placing a heat shrink tube over each of the plurality of plugs and the polymer tubes to form a first intermediate structure; heating the first intermediate structure with the heat shrink tube to form the branched connector with a plurality of cylindrical plugs; and removing the heat shrink tube from the branched connector with the plurality of cylindrical plugs. The heating embeds each of the plurality of plugs into the polymer tube, respectively, and each of the plurality of cylindrical plugs comprises the first polymer layer and the second polymer layer at least partially wrapped around a core made of the polymer tube.

In some embodiments, the first polymer layer is polyimide, liquid crystal polymer, parylene, polyether ether ketone, or a combination thereof. In some embodiments, the second polymer layer is polyimide, liquid crystal polymer, parylene, polyether ether ketone, or a combination thereof.

In some embodiments, the plurality of conductive traces and the subset of conductive traces are comprised of one or more layers of conductive material, and the conductive material is platinum (Pt), platinum/iridium (Pt/Ir), titanium (Ti), gold/titanium (Au/Ti), or any alloy thereof.

In some embodiments, each of the end portions is partially wrapped around the mandrel or the polymer tube, respectively such that the plurality of cylindrical end portions are a plurality of split cylindrical end portions, and each split cylindrical end portion of the plurality of split cylindrical end portions comprises a gap for the split having a predefined width.

In some embodiments, the method further comprises forming a third polymer layer on the second polymer layer in a region between the main body portion and the plurality of end portions. In some embodiments, the third polymer layer is silicone.

BRIEF DESCRIPTION OF THE DRAWINGS

The present invention will be better understood in view of the following non-limiting figures, in which:

FIGS. 5A-5G show an alternative lead assembly in accordance with various embodiments;

DETAILED DESCRIPTION

I. Introduction

Figure 1:
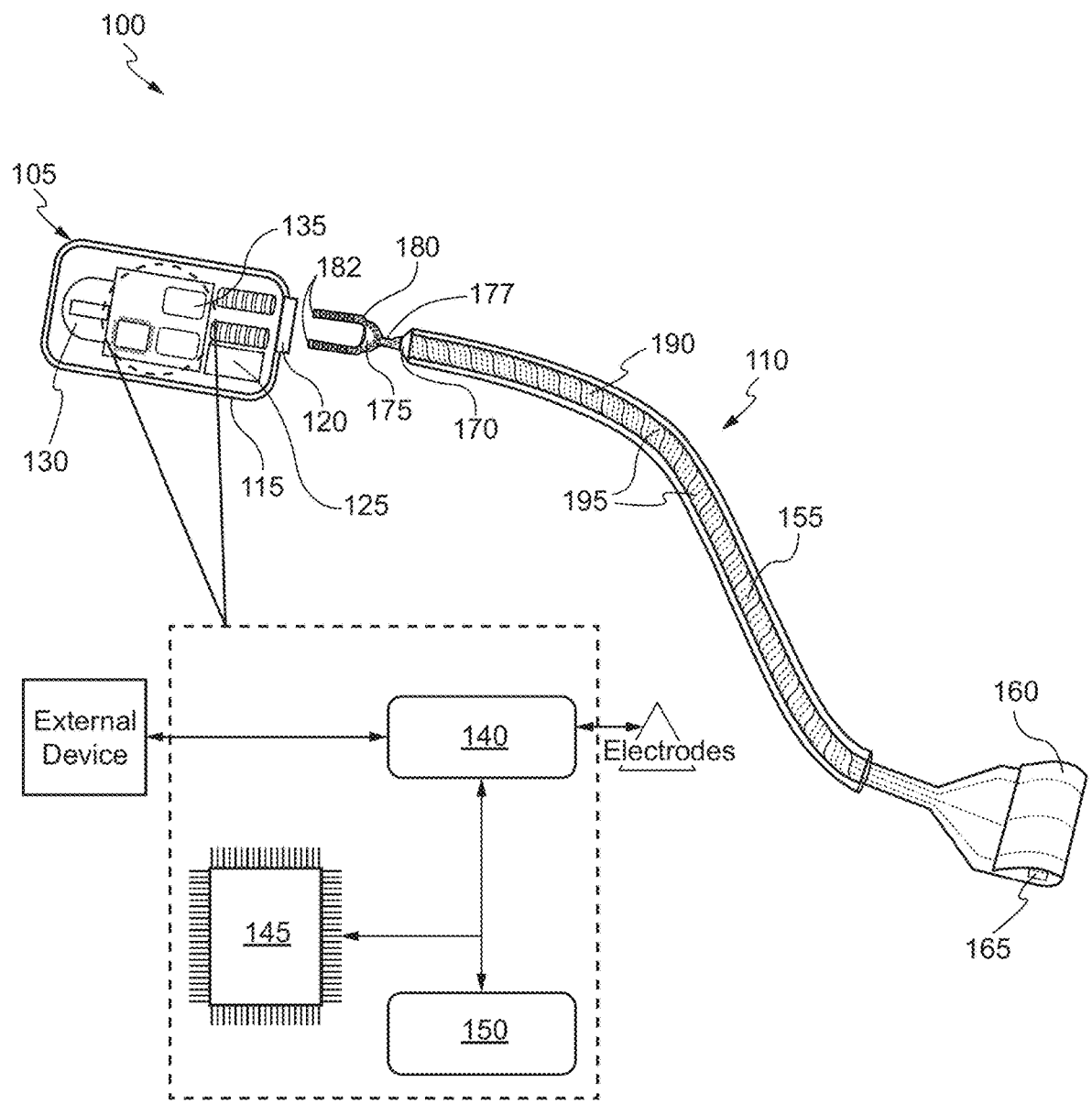
FIG. 1 shows a neuromodulation system in accordance with various embodiments.

The following disclosure describes branched proximal connectors for high density neural interfaces and methods of microfabricating the branched proximal connectors. As used herein, the phrase "branched" refers to lateral extensions or subdivisions extending from a main body. As used herein, the term "proximal" or "proximal end" refers to a first end of the main body, while the term "distal" or "distal end" refers to a second end opposing the first end. For example, the proximal end may be an end of the main body, which is closest to the user, and the distal end may be an end of the main body, which is furthest from the user. The branched proximal connector may be fabricated using microfabricating techniques. In certain embodiments, the branched connector is fabricated as a monolithic structure. As used herein, the phrase "monolithic" refers to a device fabricated using a same layer of base material. As used herein, the phrase "microfabrication" refers to the process of fabricating miniature structures on micrometer scales and smaller. The major concepts and principles of microfabrication are microlithography, doping, thin films, etching, bonding, and polishing. As used herein, the phrase "thin films" refers to a layer of material ranging from fractions of a nanometer (monolayer) to several micrometers in thickness (e.g., between a few nanometers to about 100 μm). Thin films may be deposited by applying a very thin film of material (e.g., between a few nanometers to about 100 μm) onto a substrate surface to be coated, or onto a previously deposited layer of thin film. In various embodiments, a thin film connector is provided comprising a base polymer body (e.g., a supporting structure) and at least one conductive trace formed on the base polymer body. As used herein, the term "high density neural interface(s)" refers to a neural interface that comprises at least sixteen electrodes (i.e., recording, sensing, stimulating, other types of electrodes, or combinations thereof).

Neuromodulation devices such as deep brain and spinal cord stimulators electrically interface with neural tissue and treat various neurological conditions through electrical stimulation. As described herein, conventional neuromodulation devices use between four and sixteen electrodes and comprise a neurostimulator and lead assembly containing electrodes. There is a need for high-density lead assemblies that can significantly increase the number of electrodes in order to interface with larger tissue volume, to recruit smaller populations of neurons for recording, or to provide more targeted therapy by tailoring the electrical stimulation parameters and activated tissue volume. Conventional neuromodulation devices use up to eight channels per lead assembly in an axial orientation. These devices are typically limited to no more than eight channels per lead assembly due partly to the lack of compatible connector technology. Conventional neuromodulation devices that can accommodate greater than eight channels per lead assembly are limited by a requirement of permanency of the connection to limit susceptibility of the connector to disconnections and fractures.

To address these limitations and problems, branched proximal connectors of various embodiments disclosed herein enable connections with high density neural interfaces and are capable of being physically disconnected between the neurostimulator and the lead assembly. One illustrative embodiment of the present disclosure is directed to a branched connector that includes a main body having a base portion of a supporting structure and a plurality of conductive traces formed on the base portion, and a plurality of plugs extending from the main body. The base portion of the supporting structure is comprised of one or more layers of dielectric material. Each plug of the plurality of plugs includes an end portion of the supporting structure comprised of the one or more layers of dielectric material, and a subset of conductive traces from the plurality of conductive traces. Each trace from the subset of conductive traces terminates at a bond pad exposed on a surface of the end portion of the supporting structure.

In other embodiments, a monolithic thin-film lead assembly is provided that includes a cable comprising a proximal end, a distal end, a supporting structure that extends from the proximal end to the distal end, and a plurality of conductive traces formed on a portion of the supporting structure. The supporting structure is comprised of one or more layers of dielectric material. The monolithic thin-film lead assembly further includes an electrode assembly formed on the supporting structure at the distal end of the cable. The electrode assembly comprises one or more electrodes in electrical connection with one or more conductive traces of the plurality of conductive traces. The monolithic thin-film lead assembly further includes a branched connector formed on the supporting structure at the proximal end of the cable. The branched connector comprises: (i) a main body comprising the supporting structure and the plurality of conductive traces, and (ii) a plurality of plugs extending from the main body, each plug of the plurality of plugs comprises the supporting structure and a subset of conductive traces from the plurality of conductive traces, where each trace from the subset of conductive traces terminates at a bond pad exposed on a surface of the supporting structure.

In other embodiments, a thin-film lead assembly is provided that includes a cable comprising a proximal end, a distal end, a first supporting structure that extends from the proximal end to the distal end, and a plurality of conductive traces formed on a portion of the first supporting structure. The thin-film lead assembly further includes an electrode assembly formed on the first supporting structure at the distal end of the cable. The electrode assembly comprises one or more electrodes in electrical connection with one or more conductive traces of the plurality of conductive traces. The thin-film lead assembly further includes a branched connector comprising: (i) a main body comprising a second supporting structure and a plurality of conductive connector traces, and (ii) a plurality of plugs extending from the main body, each plug of the plurality of plugs comprises the second supporting structure and a subset of conductive connecting traces from the plurality of conductive connecting traces. Each trace from the subset of conductive connecting traces terminates at a bond pad exposed on a surface of the second supporting structure. The plurality of conductive connector traces of the branched connector are in electrical contact with the plurality of conductive traces of the cable, respectively.

In other embodiments, a neuromodulation system is provided that includes a neurostimulator comprising an electronics module, a cable comprising a supporting structure and a plurality of conductive traces formed on a portion of the supporting structure, where the supporting structure is comprised of one or more layers of dielectric material, an electrode assembly formed on the supporting structure, where the electrode assembly comprises one or more electrodes in electrical connection with one or more conductive traces of the plurality of conductive traces, and a branched connector formed on the supporting structure at the proximal end of the cable. The branched connector comprises: (i) a main body comprising the supporting structure and the plurality of conductive traces, and (ii) a plurality of plugs extending from the main body, each plug of the plurality of plugs comprises the supporting structure and a subset of conductive traces from the plurality of conductive traces. The branched connector electrically connects each subset of conductive traces from the plurality of conductive traces to the electronics module.

To further address these limitations and problems, a method of manufacturing the branched connector of various embodiments disclosed herein includes process steps for creating a branched structure, which results in increased contact points, a smaller footprint, and greater design flexibility. One illustrative embodiment of the present disclosure is directed to a method of manufacturing a branched connector that comprises forming a first polymer layer on a substrate. The first polymer layer comprises a main body portion and a plurality of end portions extending from the main body portion, and the main body portion and the plurality of end portions are co-planar. The method further comprises forming a plurality of conductive traces on the main body portion in a first pattern. The first pattern maintains a first predetermined distance between each trace of the plurality of traces. The method further comprises forming a subset of conductive traces on each of the plurality of end portions in a second pattern. The second pattern maintains a second predetermined distance between each trace of the subset of traces and electrical connects each trace of the subset of traces to each trace of the plurality of traces, respectively. The method further comprises depositing a second polymer layer on the first polymer layer, the plurality of conductive traces, and each of the subset of conductive traces. The method further comprises forming at least one contact via in the first polymer layer of each of the plurality of end portions such that the at least one contact via is in electrical contact with at least one trace of the subset of conductive traces. The method further comprises forming at least on bond pad on the first polymer layer of each of the plurality of end portions such that the at least one bond pad is in electrical contact with the at least one contact via, and cutting the branched connector from the first polymer layer and the second polymer. The branched connector comprises the main body portion and the plurality of end portions extending from the main body portion.

Advantageously, these approaches provide a branched connector, which has increased contact points, a smaller footprint, and greater design flexibility. More specifically, these approaches enable branched connectors with reliable, non-permanent connections between a lead assembly and a neurostimulator. This solution is scalable to connecting many electrodes (e.g., greater than sixteen) using a multi flex chip, and thus enabling several therapeutic opportunities for neurostimulation. Furthermore even for applications where multiple electrodes are not required, various embodiments can be miniaturized to make the implant minimally invasive, additionally may make invasive anatomies to become accessible (or navigable) due to the miniaturization. It should be understood that although deep brain neurostimulation and vagus nerve or artery/nerve plexus device applications are provided as examples of some embodiments, this solution is applicable to all leads and devices that need electrodes/sensors that need to be attached to a neurostimulator.

II. Neuromodulation Devices and Systems with a Lead Assembly

FIG. 1 shows a neuromodulation system 100 in accordance with some aspects of the present invention. In various embodiments, the neuromodulation system 100 includes an implantable neurostimulator 105 and a lead assembly 110. The implantable neurostimulator 105 (e.g., an implantable pulse generator (IPG)) may include a housing 115, a feedthrough assembly 120, a power source 125, an antenna 130, and an electronics module 135 (e.g., a computing system). The housing 115 may be comprised of materials that are biocompatible such as bioceramics or bioglasses for radio frequency transparency, or metals such as titanium. In accordance with some aspects of the present invention, the size and shape of the housing 115 may be selected such that the neurostimulator 105 can be implanted within a patient. In the example shown in FIG. 1, the feedthrough assembly 120 is attached to a hole in a surface of the housing 115 such that the housing 115 is hermetically sealed. The feedthrough assembly 120 may include one or more contacts (i.e., electrically conductive elements, pins, wires, tabs, pads, etc.) mounted within the housing 115 or a cap extending from an interior to an exterior of the housing 115. The power source 125 may be within the housing 115 and connected (e.g., electrically connected) to the electronics module 135 to power and operate the components of the electronics module 135. The antenna 130 may be connected (e.g., electrically connected) to the electronics module 135 for wireless communication with external devices via, for example, radiofrequency (RF) telemetry.

In some embodiments, the electronics module 135 may be connected (e.g., electrically connected) to interior ends of the feedthrough assembly 120 such that the electronics module 135 is able to apply a signal or electrical current to conductive traces of the lead assembly 110 connected to the feedthrough assembly 120. The electronics module 135 may include discrete and/or integrated electronic circuit components that implement analog and/or digital circuits capable of producing the functions attributed to the neuromodulation devices or systems such as applying or delivering neural stimulation to a patient. In various embodiments, the electronics module 135 may include software and/or electronic circuit components such as a pulse generator 140 that generates a signal to deliver a voltage, current, optical, or ultrasonic stimulation to a nerve or artery/nerve plexus via electrodes, a controller 145 that determines or senses electrical activity and physiological responses via the electrodes and sensors, controls stimulation parameters of the pulse generator 140 (e.g., control stimulation parameters based on feedback from the physiological responses), and/or causes delivery of the stimulation via the pulse generator 140 and electrodes, and a memory 150 with program instructions operable on by the pulse generator 140 and the controller 145 to perform one or more processes for applying or delivering neural stimulation.

In various embodiments, the lead assembly 110 includes a cable or lead body 155, one or more electrode assemblies 160 having one or more electrodes 165 (optionally one or more sensors), and a branched connector 170. In some embodiments, the lead assembly 110 is a monolithic structure. In various embodiments, the branched connector 170 includes a main body 175 having a base portion of a supporting structure 177 and one or more of conductive traces 180 formed on the base portion, and a plurality of plugs 182 extending from the main body. The base portion of the supporting structure may be comprised of one or more layers of dielectric material. Each plug of the plurality of plugs includes an end portion of the supporting structure comprised of the one or more layers of dielectric material, and a subset of conductive traces 185 from the one or more of conductive traces. Each trace from the subset of conductive traces terminates at a bond pad exposed on a surface of the end portion of the supporting structure.

The cable 155 may include one or more conductive traces 190 formed on a supporting structure 195. The one or more conductive traces 190 allow for electrical coupling of the electronics module 135 to the electrodes 165 and/or sensors of the electrode assemblies 160 via the branched connector 170. In some embodiments, the one or more of conductive traces 180 are the same conductive traces as the one or more conductive traces 190 (monolithic traces). In other embodiments, the one or more of conductive traces 180 are different conductive traces from the one or more conductive traces 190 (a different structure but electrically connected). As described herein in detail, the supporting structure 177/195 may be formed with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends may be used. The conductive material for the traces 180/190 may be any suitable conductor such as stainless steel, silver, copper or other conductive materials, which may have separate coatings or sheathing for anticorrosive, insulative and/or protective reasons.

The electrode assemblies 160 may include the electrodes 165 and/or sensors fabricated using various shapes and patterns to create certain types of electrode assemblies (e.g., book electrodes, split cuff electrodes, spiral cuff electrodes, epidural electrodes, helical electrodes, probe electrodes, linear electrodes, neural probe, paddle electrodes, intraneural electrodes, etc.). In various embodiments, the electrode assemblies 160 include a base material that provides support for microelectronic structures including the electrodes 165, a wiring layer, optional contacts, etc. In some embodiments, the base material is the supporting structure 195. The wiring layer may be embedded within or located on a surface of the supporting structure 195. The wiring layer may be used to electrically connect the electrodes 165 with the one or more conductive traces 190 directly or indirectly via a lead conductor. The term "directly", as used herein, may be defined as being without something in between. The term "indirectly", as used herein, may be defined as having something in between. In some embodiments, the electrodes 165 may make electrical contact with the wiring layer by using the contacts.

III. Branched Connectors

Figure 2:
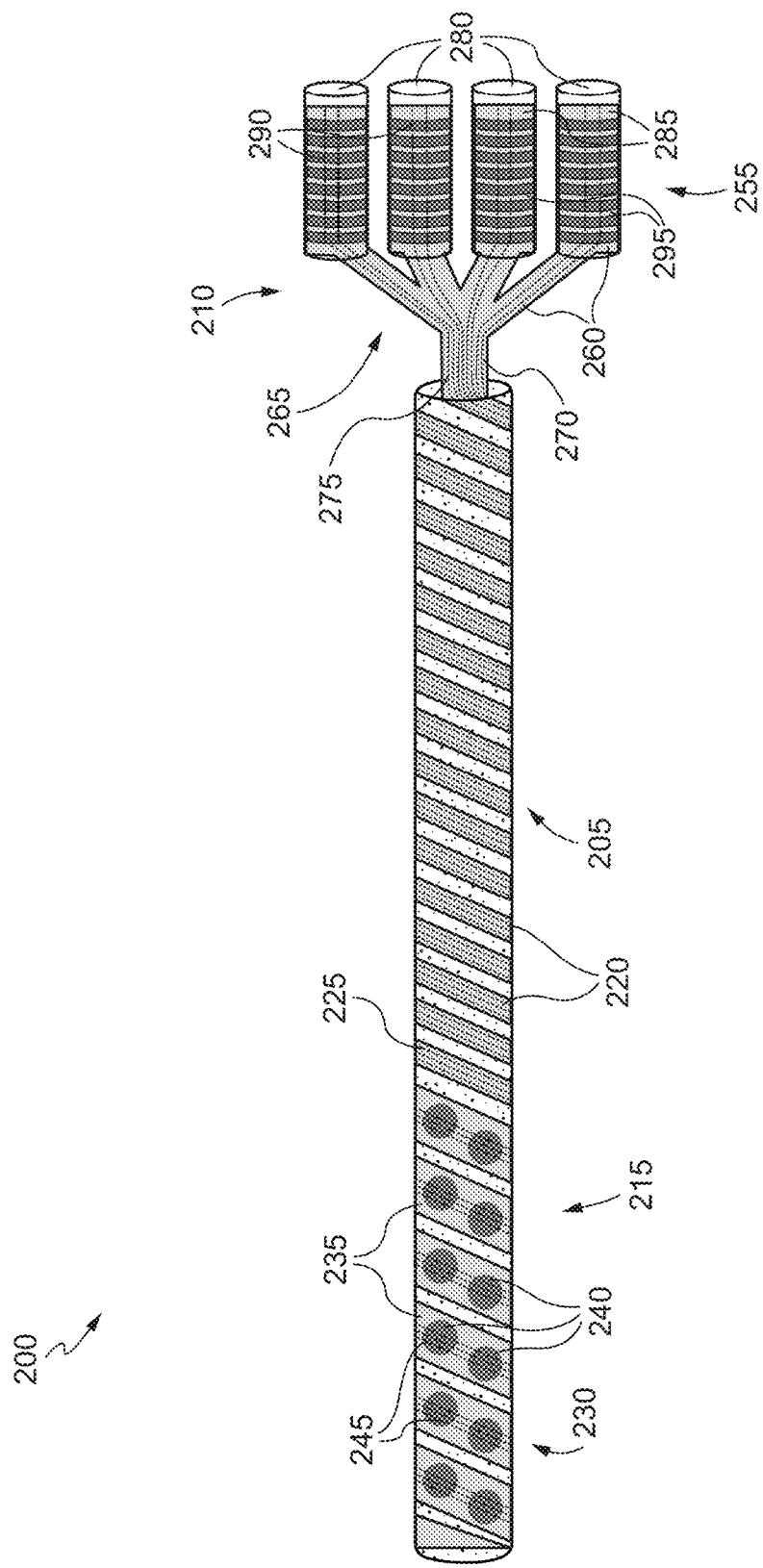
FIG. 2 shows a lead assembly in accordance with various embodiments.

FIG. 2 shows a lead assembly 200 (e.g., the lead assembly 110 described with respect to FIG. 1) in accordance with aspects of the present disclosure. In various embodiments, the lead assembly 200 comprises a cable 205 having a proximal end 210 and a distal end 215. The cable 205 may comprise a supporting structure 220 and a plurality of conductive traces 225 formed on a portion of the supporting structure 220. As used herein, the term "formed on" refers to a structure or feature that is formed on a surface of another structure or feature, a structure or feature that is formed within another structure or feature, or a structure or feature that is formed both on and within another structure or feature. In some embodiments, the supporting structure 220 extends from the proximal end 210 to the distal end 215. In some embodiments, the supporting structure 220 may be made of one or more layers of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In other embodiments, the supporting structure 220 may be made of one or more layers of dielectric material formed on a substrate. The substrate may be made from any type of metallic or non-metallic material.

In various embodiments, the one or more conductive traces 225 are a plurality of traces, for example, two or more conductive traces or from two to twenty-four conductive traces. The plurality of conductive traces 225 are comprised of one or more layers of conductive material. The conductive material selected for the one or more conductive traces 225 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the one or more conductive traces 225 have thermal expansion characteristics or a coefficient of thermal expansion (CTE) that is approximately equal to that of CTE of the supporting structure 220. Matching the CTE of components that contact one another is desirable because it eliminates the development of thermal stresses, which may occur during fabrication and the operation of the cable, and thus eliminates a known cause of mechanical failure in the components.

As shown in FIG. 2, the lead assembly 200 may further comprise an electrode assembly 230 formed on a supporting structure 235. The supporting structure 235 may provide support for microelectronic structures including one or more electrodes 240, a wiring layer 245, and optional contact(s) (not shown). The electrode assembly 230 may be located at the distal end 215 of the lead assembly 200. The one or more electrodes 240 are in electrical connection with one or more conductive traces of the plurality of conductive traces 225, for example, via the wiring layer 245 and optionally the contact(s). In various embodiments, the supporting structure 220 of the cable 205 and the supporting structure 235 of the electrode assembly 230 are the same structure (i.e., the supporting structure is continuous from the proximal end 210 to the distal end 215), which thus creates a monolithic cable. In alternative embodiments, the supporting structure 220 of the cable 205 and the supporting structure 235 of the electrode assembly 230 are different structures but are connected such that there is an electrical connection between the plurality of conductive traces 225, wiring layer 245, and the one or more electrodes 240.

As shown in FIG. 2, the lead assembly 200 may further comprise a branched connector 255 formed on a supporting structure 260. The branched connector 255 may comprise a main body 265 comprising a base portion 270 of the supporting structure 260 and one or more conductive traces 275 formed on the base portion 270. The base portion 270 of the supporting structure 260 may be comprised of one or more layers of dielectric material. In some embodiments, the supporting structure 260 may be made of one or more layers of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In other embodiments, the supporting structure 260 may be made of one or more layers of dielectric material formed on a substrate. The substrate may be made from any type of metallic or non-metallic material. In various embodiments, the supporting structure 220 of the cable 205 and the supporting structure 260 of the branched connector 255 are the same structure (i.e., the supporting structure is continuous from the proximal end 210 to the distal end 215), which thus creates a monolithic cable. In alternative embodiments, the supporting structure 220 of the cable 205 and the supporting structure 260 of the branched connector 255 are different structures but are connected such that there is an electrical connection between the plurality of conductive traces 225, wiring layer 245, the one or more electrodes 240, and the one or more conductive traces 275.

In various embodiments, the one or more conductive traces 275 are a plurality of traces, for example, two or more conductive traces or from two to twenty-four conductive traces. The plurality of conductive traces 275 are comprised of one or more layers of conductive material. The conductive material selected for the one or more conductive traces 275 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the one or more conductive traces 275 have thermal expansion characteristics or a coefficient of thermal expansion (CTE) that is approximately equal to that of CTE of the supporting structure 260. Matching the CTE of components that contact one another is desirable because it eliminates the development of thermal stresses, which may occur during fabrication and the operation of the cable, and thus eliminates a known cause of mechanical failure in the components. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

The branched connector 255 may further comprise a plurality of plugs 280 extending from the main body 265. In some embodiments, at least one plug of the plurality of plugs 280 comprises an end portion 285 of the supporting structure 260 comprised of the one or more layers of dielectric material, and a subset of conductive traces 290 from the plurality of conductive traces 275. The base portion 270 of the supporting structure 260 and each of the end portions 285 of the supporting structure 260 may be monolithic. At least one trace from the subset of conductive traces 290 may terminate at a bond pad 295 exposed on a surface of the end portion 285 of the supporting structure. In alternative embodiments, each plug of the plurality of plugs 280 comprises an end portion 285 of the supporting structure 260 comprised of the one or more layers of dielectric material, and a subset of conductive traces 290 from the plurality of conductive traces 275. Each trace from the subset of conductive traces 290 may terminate at a bond pad 295 exposed on a surface of the end portion 285 of the supporting structure. As should be understood, in some embodiments, each electrode from the one or more electrodes 240 is electrically connected via a corresponding wiring layer 245, optional contact, conductive trace 225, conductive trace 275, subset conductive trace 290, and bond pad 295 to a respective bond pad. In other words, each electrode may be electrically connected to a different bond pad (a one to one relationship). In alternative embodiments, a multiplexer chip may be used such that one or more electrodes from the one or more electrodes 240 is electrically connected via wiring layer 245, optional contact, a conductive trace 225, a conductive trace 275, and a subset conductive trace 290 to a single bond pad 295. In other words, each electrode may be electrically connected to a same or different bond pad (a many to one relationship).

The one or more conductive traces 275 and subset of conductive traces 290 may be deposited onto a surface of the supporting structure 260 by using thin film deposition techniques well known to those skilled in the art such as by sputter deposition, chemical vapor deposition, metal organic chemical vapor deposition, electroplating, electroless plating, and the like. In some embodiments, the thickness of the one or more conductive traces 275 and subset of conductive traces 290 is dependent on the particular impedance desired for conductor, in order to ensure excellent signal integrity (e.g., electrical signal integrity for stimulation or recording). For example, if a conductor having a relatively high impedance is desired, a small thickness of conductive material should be deposited onto the supporting structure 260. If, however, a signal plane having a relatively low impedance is desired, a greater thickness of electrically conductive material should be deposited onto the supporting structure 260. In certain embodiments, each of the one or more conductive traces 275 and subset of conductive traces 290 has a thickness (t). In some embodiments, the thickness (t) is from 0.5 µm to 25 µm or from 5 µm to 10 µm, for example about 5 µm or about 8 µm. In some embodiments, each of the one or more conductive traces 275 and subset of conductive traces 290 has a length (l) of about 1 mm to 100 mm or 1 cm to 3 cm, e.g., about 15 mm. In some embodiments, each of the one or more conductive traces 275 and subset of conductive traces 290 has a width (w) from 2.0 µm to 500 µm, for example about 30 µm or about 50 µm.

Figure 3:
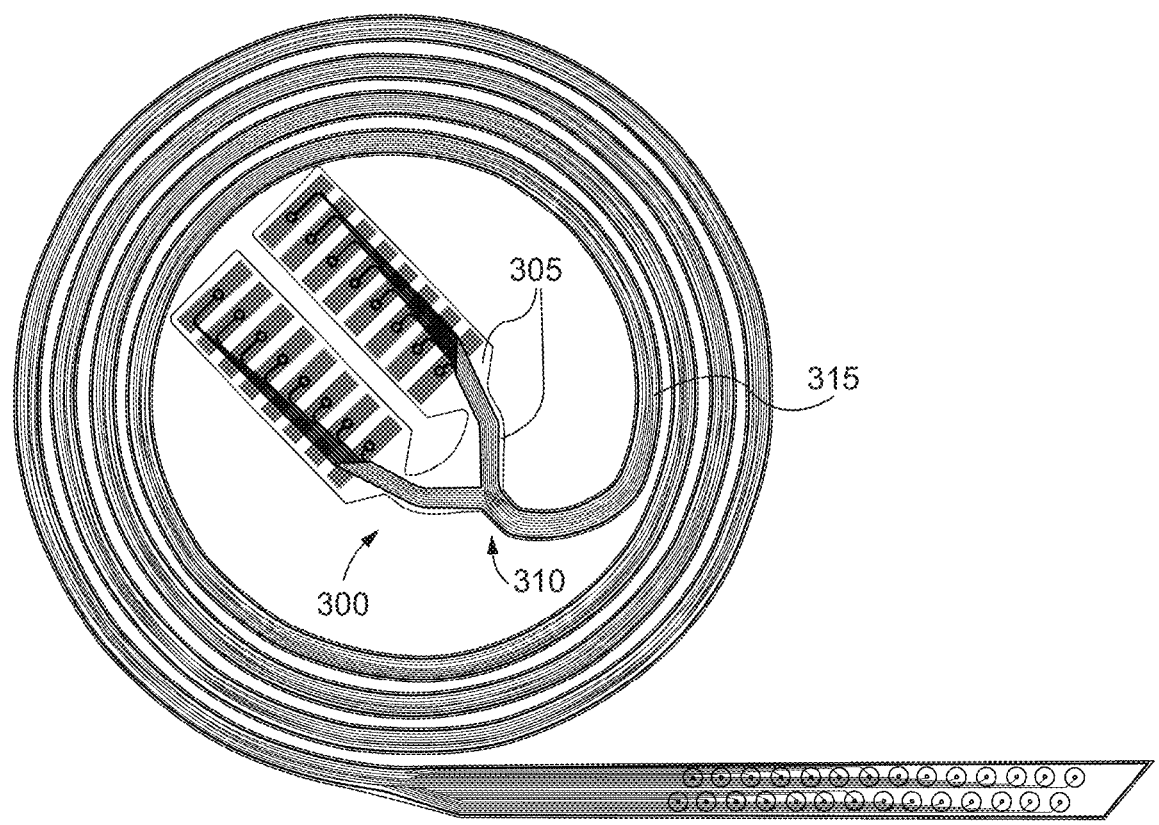
FIG. 3 shows a branched connector in accordance with various embodiments.

As shown in FIG. 3, the branched connector 300 (e.g., the branched connector 255 as discussed with respect to FIG. 2) may be formed on a supporting structure 305 at the proximal end 310 of a cable 315 with a predetermined shape in accordance with aspects of the present disclosure. In particular, as described in greater detail herein, the branched connector 300 may be formed with a predetermined shape from a prefabricated wafer or panel of dielectric material or optionally a substrate. For example, the branched connector 300 may be laser cut from a prefabricated wafer or panel in a bifurcated or multi-branched shape. Two branches are shown (bifurcated) in some of the figures but it should be understood that more than two branches can be used (multi-branched). The bifurcated or multi-branched shape may include characteristics designed to minimize the footprint of the connector while maximizing the number of contacts or bond pads that can be fabricated for the connector.

Figure 4A:
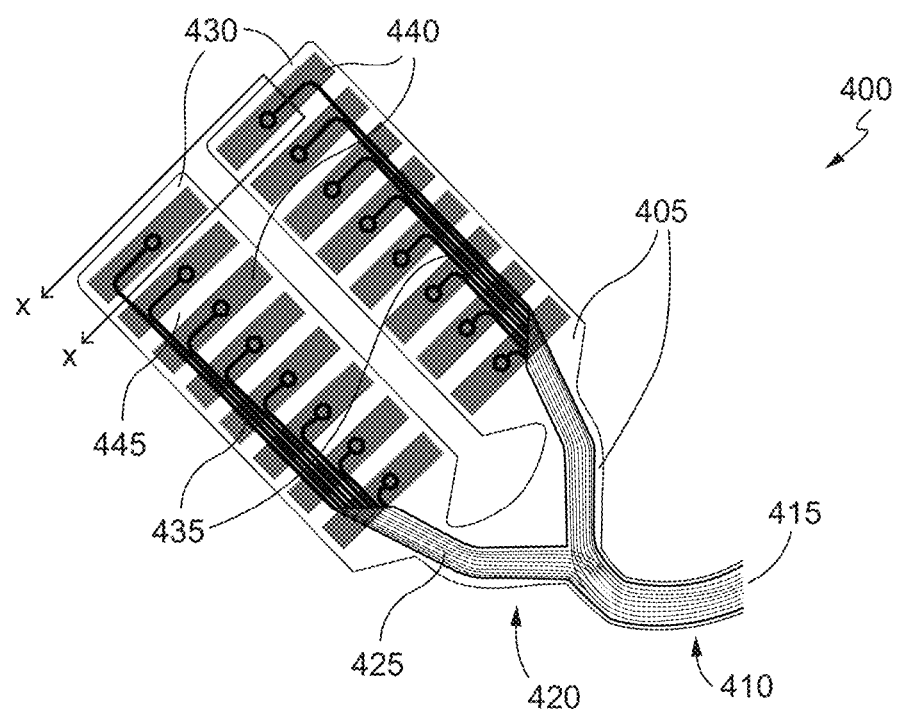
FIG. 4A shows an enlarged view of the branched connector in accordance with various embodiments.

In some embodiments, as shown in FIG. 4A, the branched connector 400 may be formed on a supporting structure 405 at the proximal end 410 of a cable 415. The branched connector 400 may comprise: (i) a main body 420 comprising the supporting structure 405 and a plurality of conductive traces 425, and (ii) a plurality of plugs 430 extending from the main body 420. Each plug of the plurality of plugs 430 may comprise the supporting structure 405 and a subset of conductive traces 435 from the plurality of conductive traces 425. Each trace from the subset of conductive traces 435 may terminate at a bond pad 440 exposed on a surface 445 of the supporting structure 405. As illustrated in FIG. 4A, one or more of the plugs 430 (or ends of the supporting structure) are planar. In some embodiments, each of the plugs 430 (or ends of the supporting structure) are planar. A used herein, "planar" means relating to or in the form of a plane. In some embodiments, two or more of the plugs 430 (or ends of the supporting structure) are coplanar with one another. In some embodiments, one or more of the plugs 430 (or ends of the supporting structure) are coplanar with the main body. As used herein, "coplanar" means in the same plane.

Figure 4B:
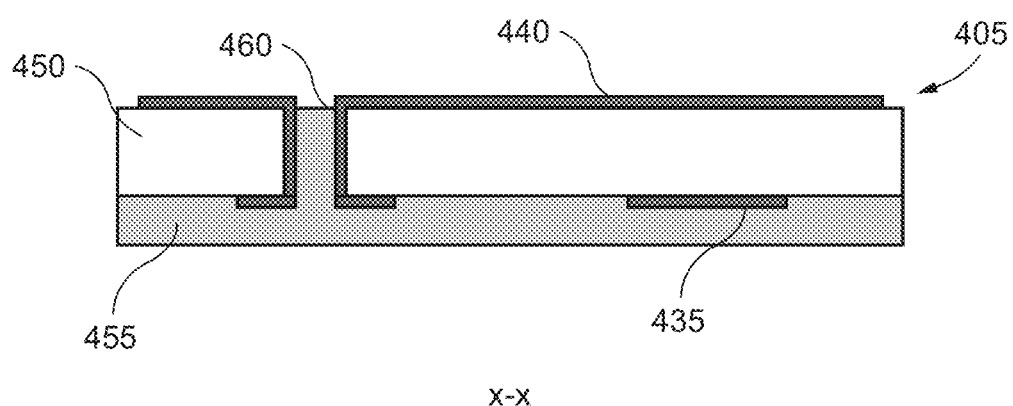
FIG. 4B shows a cross-section of the branched connector in accordance with various embodiments.
Figure 5F:
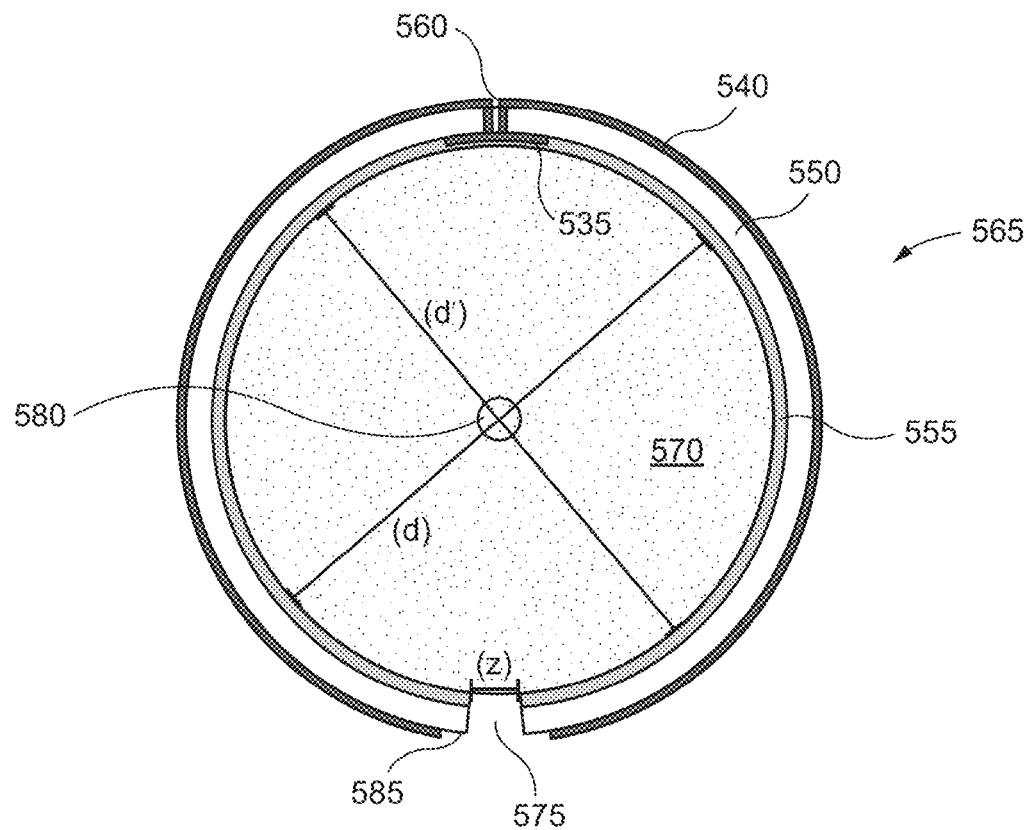

As shown in FIG. 4B (cross-section of a plug 430 along X-X from FIG. 4A), the supporting structure 405 of each of the plugs 430 comprises a first layer of dielectric material 450 and a second layer of dielectric material 455 with the subset of conductive traces 435 buried between the first layer of dielectric material 450 and the second layer of dielectric material 455. In some embodiments, the first layer of dielectric material 450 comprises at least one contact via 460 for each bond pad 440. The contact via 460 may comprise a conductive material for electrically connecting each bond pad 440 to at least one trace of the subset of conductive traces 435 such that each trace from the subset of conductive traces 435 terminates at a bond pad 440. The contact via 460 may be connected to the at least one trace of the subset of conductive traces 435 directly or indirectly by way of a wiring layer (not shown). In some embodiments, the conductive material is lined on at least a portion of the walls of the via hole. In other embodiments, the conductive material fills the via hole. In some embodiments, the first layer of dielectric material 450 is a high temperature liquid crystal polymer, and the second layer of dielectric material 455 is a low temperature liquid crystal polymer. As used herein, "a high temperature liquid crystal polymer" refers to a liquid crystal polymer with a high melting temperature of greater than 300° C. As used herein, "a low temperature liquid crystal polymer" refers to a liquid crystal polymer with a low melting temperature of less than 300° C. In other embodiments, as shown in FIGS. 5A, 5B, 5C, 5F, and 5G, the branched connector 500 may be formed on a supporting structure 505 at the proximal end 510 of a cable 515. The branched connector 500 may comprise: (i) a main body 520 comprising the supporting structure 505 and a plurality of conductive traces 525, and (ii) a plurality of plugs 530 extending from the main body 520. Each plug of the plurality of plugs 530 may comprise the supporting structure 505 and a subset of conductive traces 535 from the plurality of conductive traces 525. Each trace from the subset of conductive traces 535 may terminate at a bond pad 540 exposed on a surface 545 of the supporting structure 505. As illustrated in FIG. 5F, one or more of the plugs 530 (or ends of the supporting structure) are a cylindrical tube 565. Although the plugs are described herein with respect to a cylindrical tube shape, it should be understood that other shapes for the plugs have been contemplated, for example, spherical cubed, torus, ellipsoid, etc. In some embodiments, each of the plugs 530 (or ends of the supporting structure) is a cylindrical tube 565. A used herein, "cylindrical" means having straight parallel sides and a circular or oval cross-section; in the shape or form of a cylinder.

Figure 5G:
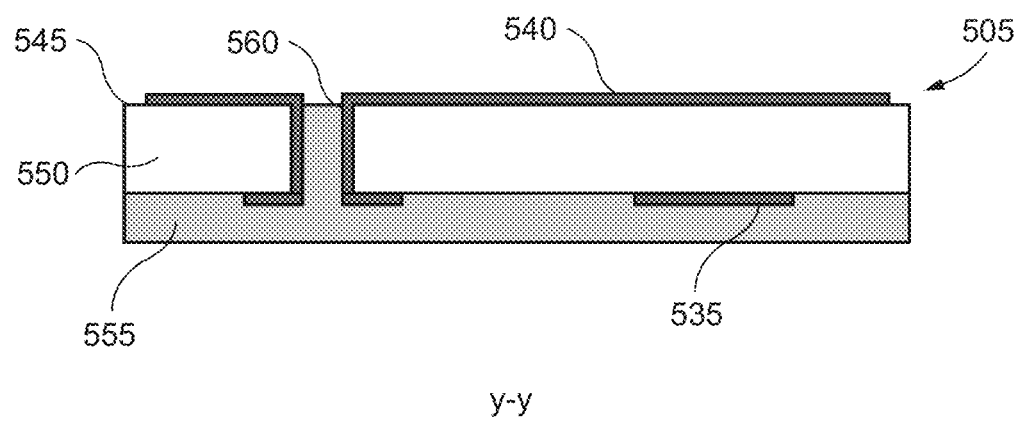

As shown in FIG. 5G (cross-section of a plug 530 along Y-Y from FIG. 5B), the supporting structure 505 of each of the plugs 530 comprises a first layer of dielectric material 550 and a second layer of dielectric material 555 with the subset of conductive traces 535 buried between the first layer of dielectric material 550 and the second layer of dielectric material 555. In some embodiments, the first layer of dielectric material 550 comprises at least one via contact 560 for each bond pad 540. The via contact 560 may comprise a conductive material for electrically connecting each bond pad 540 to at least one trace of the subset of conductive traces 530 such that each trace from the subset of conductive traces 530 terminates at a bond pad 540. The via contact 560 may be connected to the at least one trace of the subset of conductive traces 530 directly or indirectly by way of a wiring layer (not shown). In some embodiments, the conductive material is line on at least a portion of the walls of the via hole. In other embodiments, the conductive material fills the via hole. In some embodiments, the first layer of dielectric material 550 is a high temperature liquid crystal polymer, and the second layer of dielectric material 555 is a low temperature liquid crystal polymer.

As shown in FIG. 5F, cylindrical tube 565 comprises the one or more layers of dielectric material 550/555. The first layer of dielectric material 550 may define an outer diameter (d) of the cylindrical tube 565 and the second layer of dielectric material 555 may define an inner diameter (d') of the tube. The cylindrical tube 565 may further comprise a core 570 that at least partially fills an interior of the cylindrical tube 565 defined by the inner diameter (d') of the cylindrical tube 565. The core 570 may be comprised of one or more layers of material such that the core 570 has a Shore durometer of greater than 70D. In some embodiments, the one or more layers of material of the core 570 is polyimide, liquid crystal polymer, parylene, polyether ether ketone, polyurethane, metal, or a combination thereof. In certain embodiments, the one or more layers of material of the core 570 is a thermosetting or thermoplastic polyurethane. The one or more layers of dielectric material 550/555 may be at least partially wrapped around the core 570. In certain embodiments, the one or more layers of dielectric material 550/555 are formed as a split cylindrical tube wrapped around the core 570, and the split cylindrical tube comprises a gap 575 for the split having a predefined width (z). The predefined width may be between 0.1 mm and 10 mm, for example about 2 mm.

As shown in FIGS. 5A, 5B, 5C, and 5F, in some embodiments, the one or more of the bond pads 540 are a split annular ring positioned around an axis 580 of the cylindrical tube 565 and exposed on the surface 585 of the cylindrical tube 565. Each split annular ring may spaced apart from one another on the surface 585 of the cylindrical tube 565 by a region 590 of the first layer of the dielectric material 550. A width (p) of the region 590 of the first layer of the dielectric material 550 that separates each split annular ring may be between 1.0 mm to 10 mm, for example about 3 mm. In some embodiments, each split annular ring connects to a single trace from the subset of conductive traces 530. In other embodiments, each split annular ring connects to two or more traces from the subset of conductive traces 530. For example, a left side of the split annular ring may be connected with a first trace and a right side of the annular ring may be connected with a second trace. Alternatively, a multiplexer chip may be used to drive signals and thus the split annular ring may be connected to multiple traces from the conductive traces 530. In various embodiments, eight bond pads 540 or split annular rings are positioned around the axis 580 of each cylindrical tube 565 and exposed on the surface 585 of each cylindrical tube 565; however, it should be understood that more or less than eight bond pads 540 or split annular rings can be positioned on the cylindrical tubes 565. For example, each cylindrical tube 565 can have the same or a different amount of bond pads 540 or split annular rings (1, 2, 3, 4, 5, 6, 7, 8, 9, 10, 11, etc.) to enhance design flexibility for the branched connector 500.

As shown in FIGS. 5A-5F, in various embodiments, the branched connector 500 may be part of a monolithic thin-film lead assembly 592 that comprises the cable 515 and an electrode assembly 594 (e.g., the cable 205 and electrode assembly 230 discussed with respect to FIG. 2). In some embodiments, the supporting structure of the cable 593 and the supporting structure of the branched connector 255 are the same structure (i.e., the supporting structure is continuous from the proximal end 210 to the distal end 215), which thus creates a monolithic cable. The branched connector 500 may include a stylet lumen 595 that is either integral with a lumen of the cable 593 or a connected extension of the lumen of the cable 593. The stylet lumen 595 provides compatibility with existing surgical techniques where a lead assembly 592 is implanted by sliding a rigid stylet through the center of the cable 593.

While the branched connectors have been described at some length and with some particularity with respect to a specific design and/or performance need, it is not intended that the branched connectors be limited to any such particular design and/or performance need. Instead, it should be understood the branched connectors described herein are exemplary embodiments, and that the branched connectors are to be construed with the broadest sense to include variations of the specific design and/or performance need described herein, as well as other variations that are well known to those of skill in the art. In particular, the shape and location of components and layers in the branched connectors may be adjusted or modified to meet specific design and/or performance needs. Furthermore, it is to be understood that other structures have been omitted from the description of the branched connectors for clarity. The omitted structures may include insulating layers, interconnect components, passive devices, etc.

IV. Methods for Fabricating Branched Connectors

FIGS. 6A-6M show structures and respective processing steps for fabricating a flexible printed circuit board 600 (e.g., as described with respect to FIGS. 2, 3, 4A, 4B, and 5A-5G) in accordance with various aspects of the invention. It should be understood by those of skill in the art that the flexible printed circuit board 600 can be manufactured in a number of ways using a number of different tools. In general, however, the methodologies and tools used to form the structures of the various embodiments can be adopted from integrated circuit (IC) technology. For example, the structures of the various embodiments, e.g., supporting structure, conductive traces, electrodes, sensors, wiring layers, bond/contact pads, etc., may be built with or without a substrate and realized in films of materials patterned by photolithographic processes. In particular, the fabrication of various structures described herein may typically use three basic building blocks: (i) deposition of films of material on a substrate and/or previous film(s), (ii) applying a patterned mask on top of the film(s) by photolithographic imaging, and (iii) etching the film(s) selectively to the mask.

As used herein, the term "depositing" may include any known or later developed techniques appropriate for the material to be deposited including but not limited to, for example: chemical vapor deposition (CVD), low-pressure CVD (LPCVD), plasma-enhanced CVD (PECVD), semi-atmosphere CVD (SACVD) and high density plasma CVD (HDPCVD), rapid thermal CVD (RTCVD), ultra-high vacuum CVD (UHVCVD), limited reaction processing CVD (LRPCVD), metalorganic CVD (MOCVD), sputtering deposition, ion beam deposition, electron beam deposition, laser assisted deposition, thermal oxidation, thermal nitridation, spin-on methods, physical vapor deposition (PVD), atomic layer deposition (ALD), chemical oxidation, molecular beam epitaxy (MBE), plating (e.g., electroplating), or evaporation.

Figure 6A:
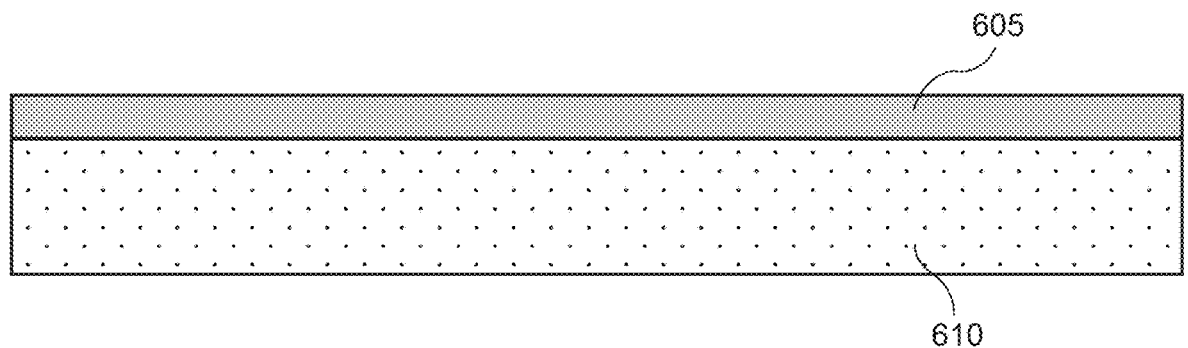
FIGS. 6A-6M show cross-sectional side views and top views illustrating a method of fabricating a flexible printed circuit board in accordance with various embodiments.

FIG. 6A shows a cross-section of a beginning structure (a supporting structure) comprising a first polymer layer 605 overlying an optional substrate 610 (e.g., a backer). In some embodiments, the beginning structure may be provided, obtained, or fabricated as a single wafer or panel having a diameter, length, and/or width of less than 15 cm. In other embodiments, the beginning structure may be provided, obtained, or fabricated for a reel-to-reel process where the substrate is long and big to reduce costs. For example, panels may be used that are at least 20×23 cm rectangles. The substrate 610 may be comprised of any type of metallic or non-metallic material. For example, the substrate 610 may be comprised of but not limited to silicon, germanium, silicon germanium, silicon carbide, and those materials consisting essentially of one or more Group III-V compound semiconductors having a composition defined by the formula $Al_{X1}Ga_{X2}In_{X3}As_{Y1}P_{Y2}N_{Y3}Sb_{Y4}$, where X1, X2, X3, Y1, Y2, Y3, and Y4 represent relative proportions, each greater than or equal to zero and $X1+X2+X3+Y1+Y2+Y3+Y4=1$ (1 being the total relative mole quantity). Substrate 610 may additionally or alternatively be comprised of Group II-VI compound semiconductors having a composition $Zn_{A1}Cd_{A2}Se_{B1}Te_{B2}$, where A1, A2, B1, and B2 are relative proportions each greater than or equal to zero and $A1+A2+B1+B2=1$ (1 being a total mole quantity). The processes to provide, obtain, or fabricate substrate 610, as illustrated and described, are well known in the art and thus, no further description is provided herein.

Figure 6B:
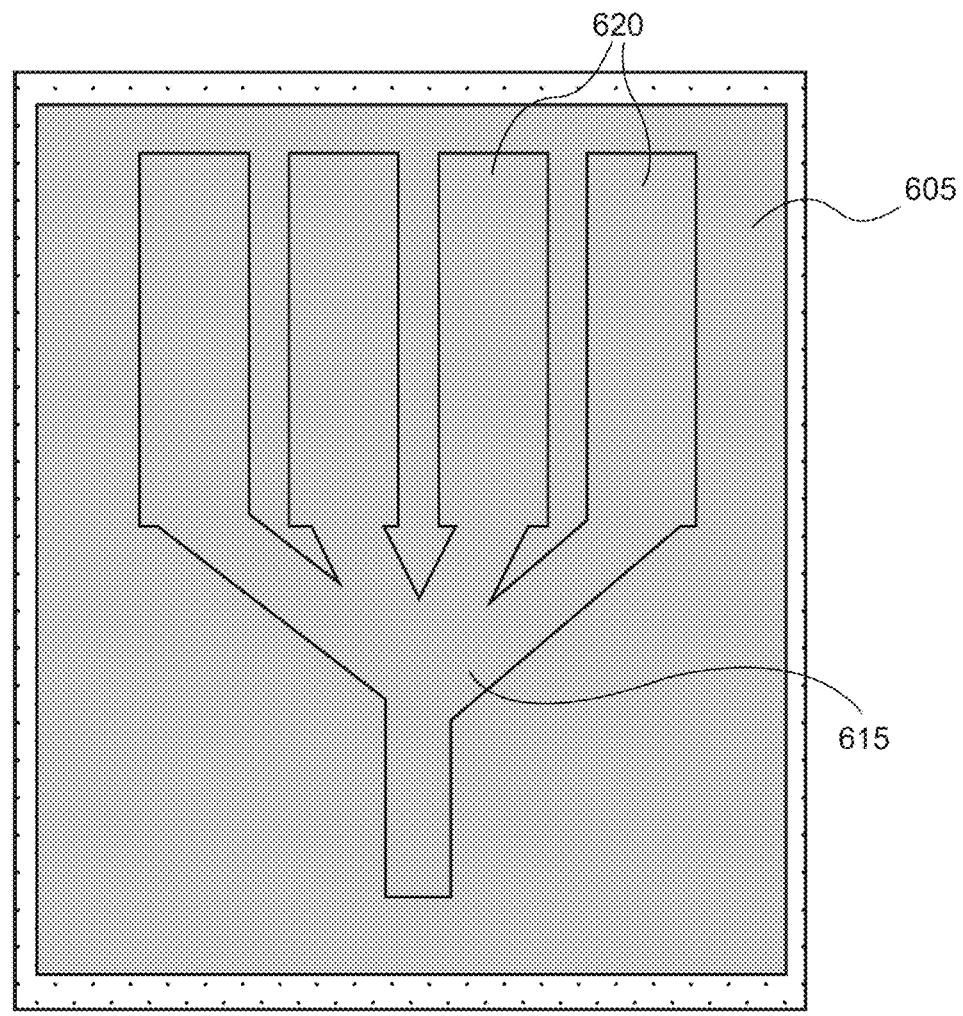

The first polymer layer 605 may be comprised of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a thermoplastic or thermosetting polymer. For example, the polymer may be a polyimide, a LCP, parylene, a PEEK, or combinations thereof. The forming of the first polymer layer 605 may include depositing and curing a dielectric material directly on the substrate 610 without an adhesion promoter. For example, a solution comprised of an imidizable polyamic acid compound dissolved in a vaporizable organic solvent without an adhesion promoter may be deposited (e.g., spin coated) onto the substrate 610. The solution may then be heated at a temperature, preferably less than 250° C., to imidize the polyamic acid compound to form the desired polyimide and vaporize the solvent. The first polymer layer 605 may then be thinned to a desired thickness by planarization, grinding, wet etch, dry etch, oxidation followed by oxide etch, or any combination thereof. This process can be repeated to achieve a desired thickness for the first polymer layer 605. In some embodiments, the first polymer layer 605 may have a thickness from 10 µm to 150 µm. In some embodiments, the first polymer layer 605 may have a thickness from 25 µm to 100 µm. In some embodiments, the first polymer layer 605 may have a thickness from 35 µm to 75 µm. FIG. 6B shows a top view of the beginning structure, which illustrates the first polymer layer 605 may comprise a main body portion 615 and a plurality of end portions 620 extending from the main body portion 605. In some embodiments, the main body portion 615 and the plurality of end portions 620 are coplanar.

Figure 6C:
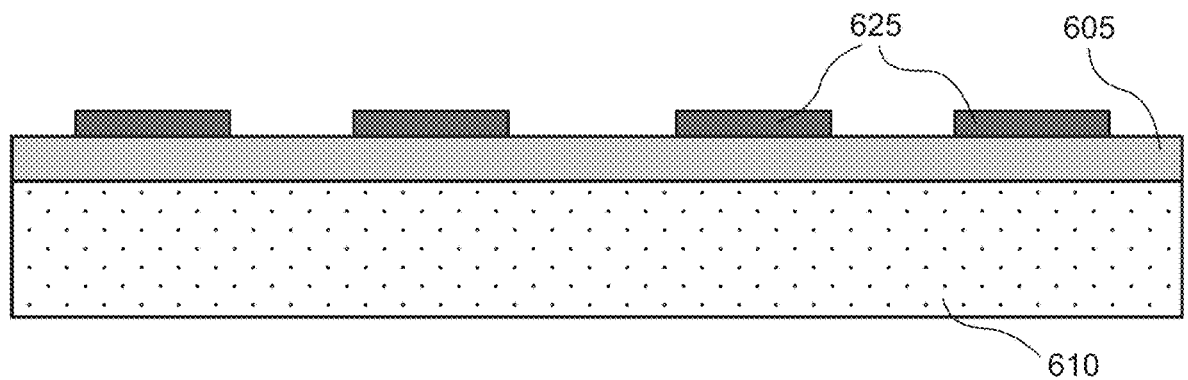

FIG. 6C shows conductive traces 625 formed in a first pattern on the main body portion 615 of the first polymer layer 605. In some embodiments, forming the conductive traces 625 includes depositing a seed layer (e.g., a platinum (Pt) seed layer, platinum/iridium (Pt/Ir) seed layer, etc.) over the first polymer layer 605. The seed layer may be configured to enable forming of a conductive trace on the first polymer layer 605 (e.g., through platinum (Pt) electroplating, platinum/iridium (Pt/Ir) electroplating, etc.). Optionally, and prior to forming of the seed layer, an adhesion layer may be deposited over the first polymer layer 605 to enable adequate application of the seed layer. Deposition of either or both of the adhesion layer and seed layer may include sputter deposition Following deposition of the seed layer, a resist pattern may be formed above the first polymer layer 605. The resist pattern may include openings that align over at least a portion of the first polymer layer 605 for forming of a plurality of conductive traces 625 (e.g., a conductive layer with a cross-sectional thickness of 0.5 µm to 100 µm or from 25 µm to 50 µm) on the first polymer layer 605. For example, the resist may be patterned with openings to form: (i) a first conductive trace 625 over a first region of the first polymer layer 605, (ii) a second conductive trace 625 over a second region of the first polymer layer 605, (iii) a third conductive trace 625 over a third region of the first polymer layer 605, and (iv) a fourth conductive trace 625 over a fourth region of the first polymer layer 605. In various embodiments, the openings of the resist may have the first pattern, which maintains a first predetermined distance between each trace of the conductive traces 625. The first pattern may include characteristics designed to minimize the foot print of the flexible printed circuit board 600. Although only, four conductive traces are described with respect to the processes discussed above, it should be understood that any number of individual conductive traces can be deposited onto the first polymer. For example, each of the four conductive traces described above could actually comprise four separate conductive traces to provide a total of sixteen conductive traces that are individually connected with contact pads described herein (see, e.g., step 6J).

In various embodiments, the conductive traces 625 may be deposited through electroplating (e.g., through Cu electroplating, Au electroplating, Sn electroplating, Ag electroplating, Au/Cr electroplating, etc.) and may be positioned over at least a portion of the first polymer layer 605 (e.g., the first region, the second region, the third region, and the fourth region). The electroplating maybe performed at a current density of about 4.0 mA/cm2 to about 4.5 mA/cm2. In some embodiments, the exposed area or portion of the first polymer layer 605 may encompass about 2 $cm^2$ to about 8 $cm^2$. The current may be about 14 mA to about 18 mA and the duration may be from about 110 minutes to about 135 minutes to form the conductive traces 625 having a thickness of about 8 μm to about 10 μm. In other embodiments, the exposed area or portion of the first polymer layer 605 may encompass about 1 $cm^2$ to about 12 $cm^2$. The current may be about 18 mA to about 28 mA and the duration may be from about 35 minutes to about 50 minutes to form the wiring layer 625 having a thickness of about 2 μm to about 5 μm.

Figure 6D:
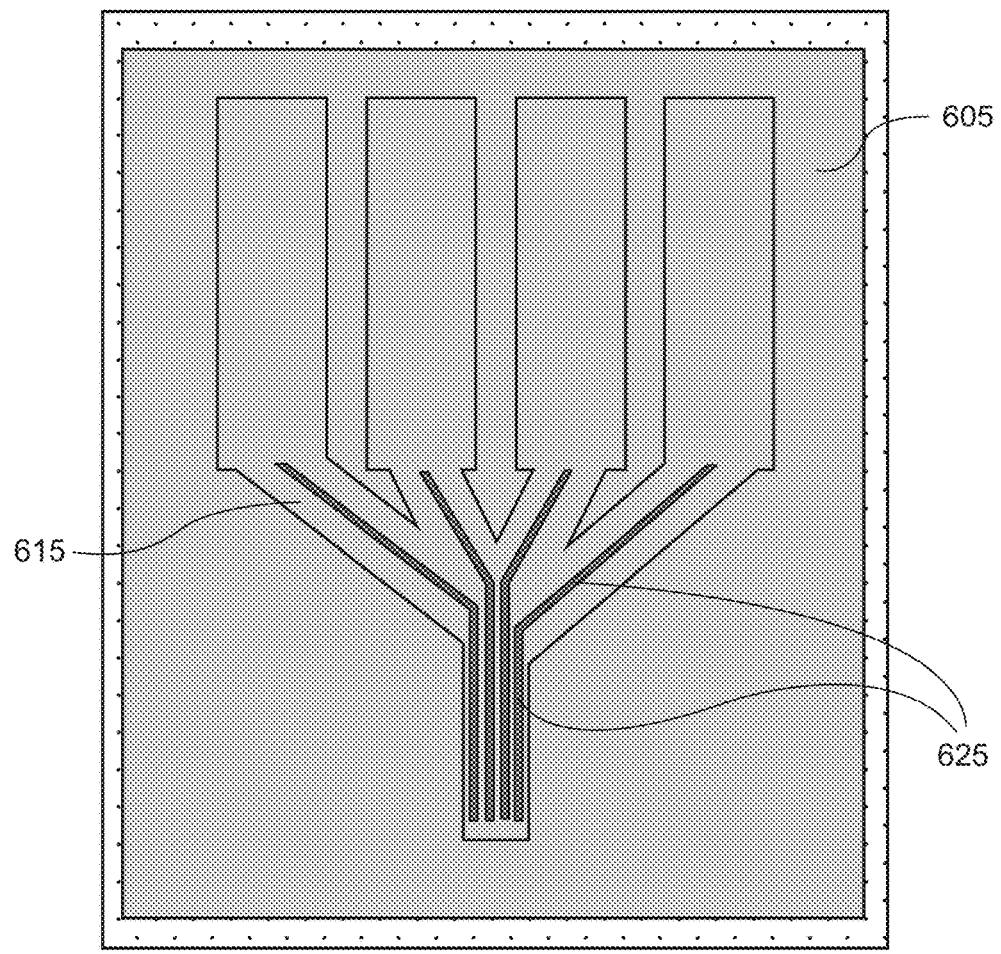

Following the deposition of the conductive traces 625, the intermediate structure may be subjected to a strip resist to remove the resist pattern and expose portions of the seed layer (portions without wire formation), and optionally the adhesion layer. The exposed portions of the seed layer, and optionally the adhesion layer, may then be subjected to an etch (e.g., wet etch, dry etch, etc.) to remove those portions, thereby isolating the conductive traces 625 over at least a portion of the first polymer layer 605. FIG. 6D shows a top view of the conductive traces 625 formed in the first pattern on the main body portion 615 of the first polymer layer 605.

Figure 6E:
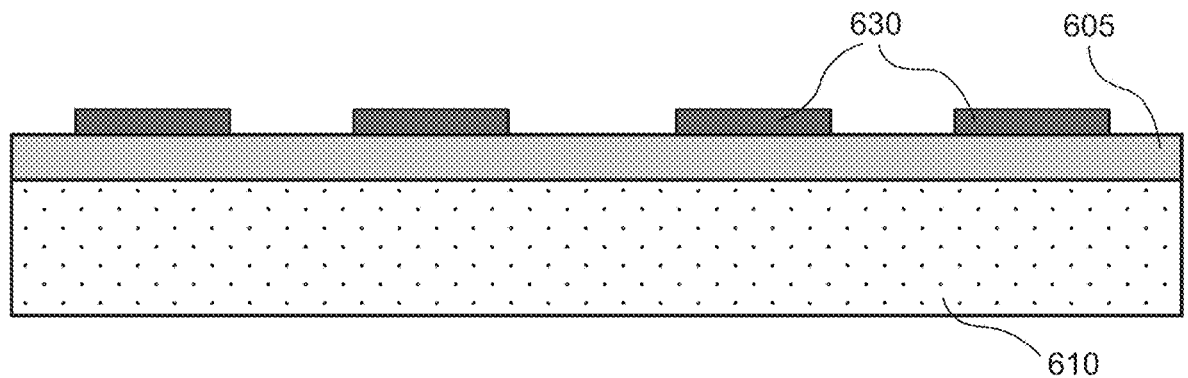
Figure 6F:
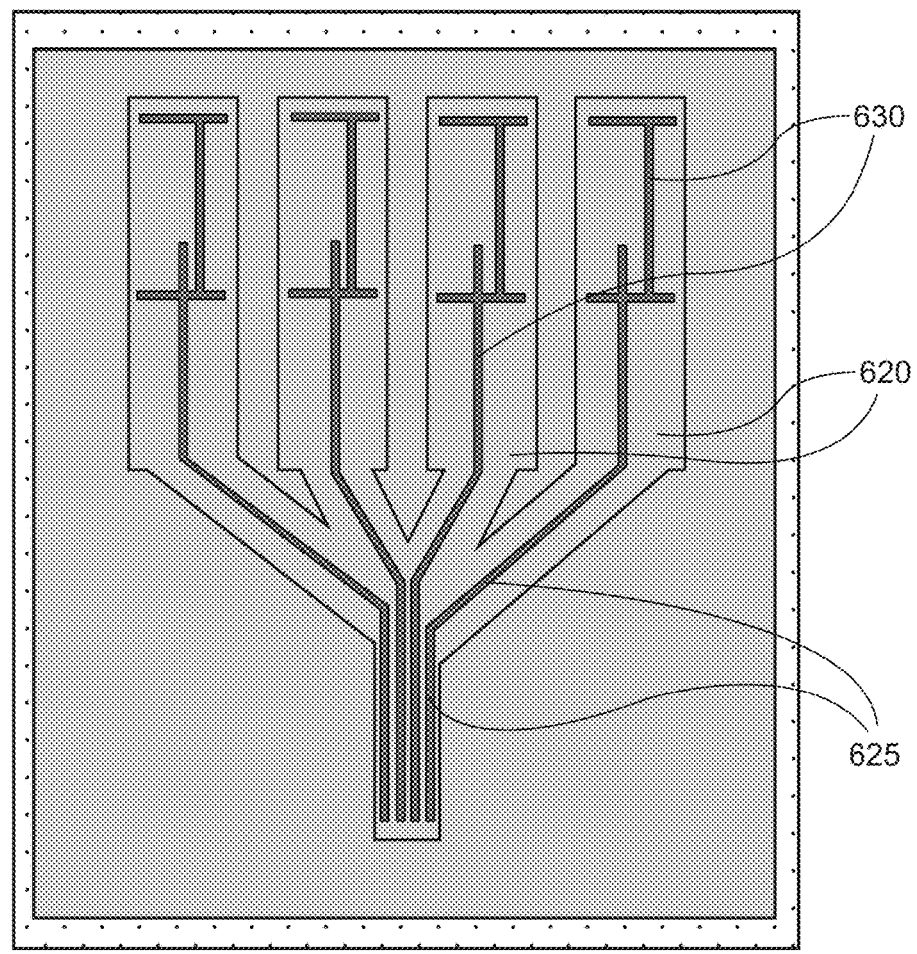

FIG. 6E shows a subset of conductive traces 630 formed on each of the plurality of end portions 620 in a second pattern. In some embodiments, the subset of conductive traces 630 are formed in manner similar described with respect to the conductive traces 625, and thus is not repeated here. In certain embodiments, the subset of conductive traces 630 may be formed in conjunction or simultaneously with the conductive traces 625. In other embodiments, the subset of conductive traces 630 may be formed subsequent to the conductive traces 625. In various embodiments, the openings of the resist may have the second pattern, which maintains a second predetermined distance between each trace of the subset of conductive traces 630. The second pattern electrical connects each trace of the subset of traces 630 to each trace of the plurality of traces 625, respectively. In some embodiments, first pattern and the second pattern are the same. In other embodiments, the first pattern and the second pattern are different. Likewise, the first predetermined distance and the second predetermined distance may be the same or different. The second pattern may include characteristics designed to minimize the foot print of the flexible printed circuit board 600 and maximize the number of contacts possible with each branch. FIG. 6F shows a top view of the subset of conductive traces 630 formed on each of the plurality of end portions 620 in a second pattern.

Figure 6G:
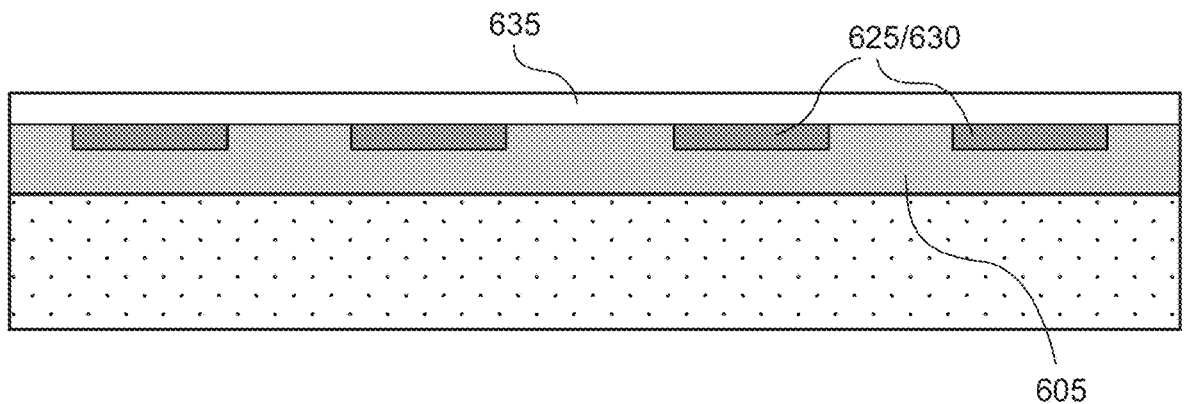

FIG. 6G shows a second polymer layer 635 formed on the first polymer layer 605, the plurality of conductive traces 625, and each of the subset of conductive traces 630. The second polymer layer 635 may be comprised of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a thermoplastic or thermosetting polymer. For example, the polymer may be a polyimide, a LCP, silicone, parylene, a PEEK, or combinations thereof. The second polymer layer 635 may be comprised of the same material or a different material from that of the first polymer layer 605. For example, the first layer of dielectric material may be a high temperature liquid crystal polymer, and the second layer of dielectric material may be a low temperature liquid crystal polymer.

Figure 6H:
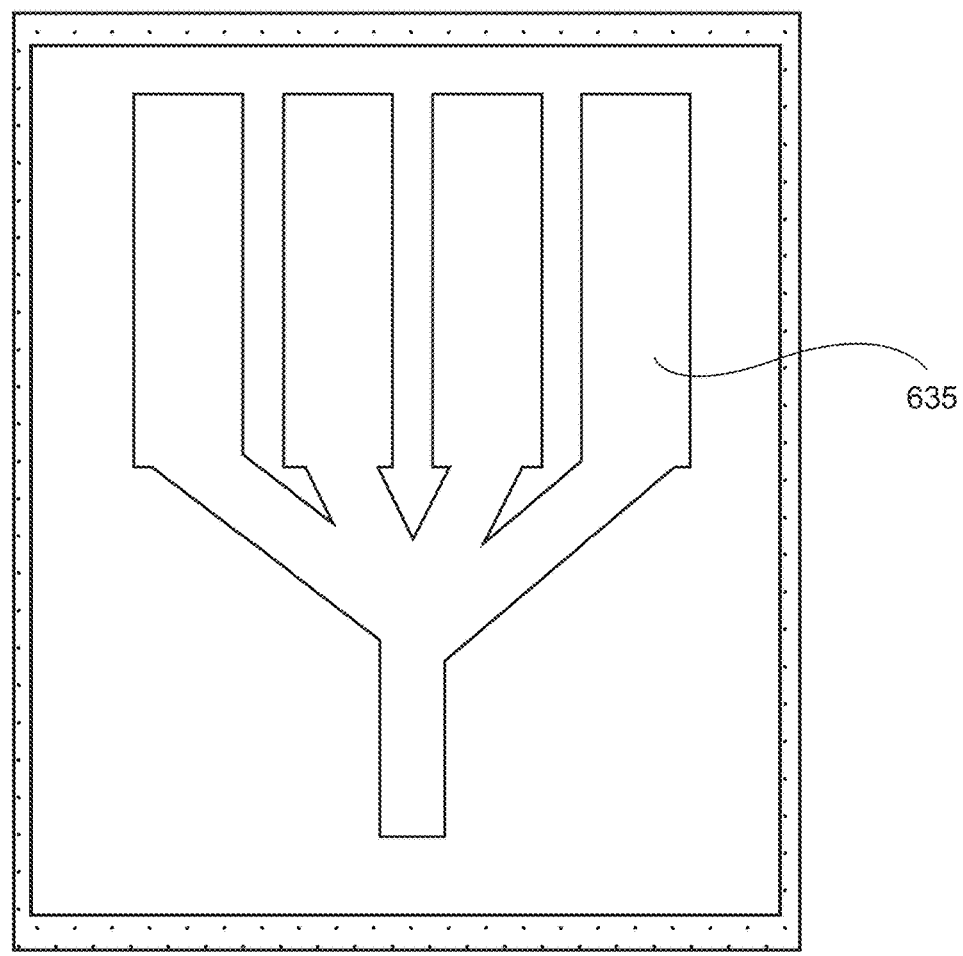

The forming of the second polymer layer 635 may include depositing and curing of a polymer material directly on the first polymer layer 605, the plurality of conductive traces 625, and each of the subset of conductive traces 630. For example, a solution comprised of an imidizable polyamic acid compound dissolved in a vaporizable organic solvent may be applied to the first polymer layer 605, the plurality of conductive traces 625, and each of the subset of conductive traces 630. The solution may then be heated at a temperature, preferably less than 250° C., to imidize the polyamic acid compound to form the desired polyimide and vaporize the solvent. The second polymer layer 635 may then be thinned to a desired thickness by planarization, grinding, wet etch, dry etch, oxidation followed by oxide etch, or any combination thereof. This process can be repeated to achieve a desired thickness for the second polymer layer 635. In some embodiments, the second polymer layer 635 may have a thickness from 1.0 μm to 50.0 μm. In some embodiments, the second polymer layer 635 may have a thickness from 4.0 μm to 15.0 μm. In some embodiments, the second polymer layer 635 may have a thickness from 5.0 μm to 7.0 μm. FIG. 6H shows a top view of the second polymer layer 635 formed on the first polymer layer 605, the plurality of conductive traces 625, and each of the subset of conductive traces 630.

Figure 6I:
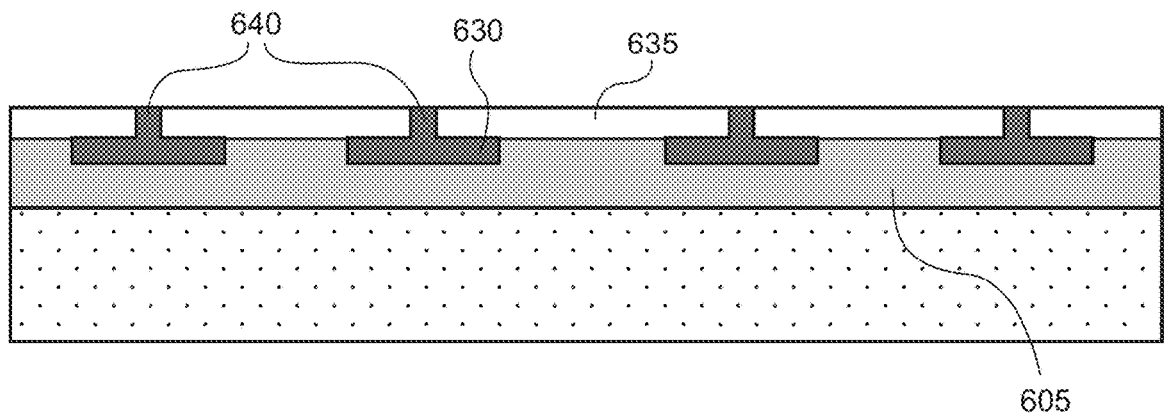

In various embodiments, the flexible printed circuit board 600 may further comprise one or more contact vias 640 and one or more bond pads 645 that support electrical connection with the electronics module of the neurostimulator. FIG. 6I shows forming at least one contact via 645 on the second polymer layer 635 formed in FIG. 6G that is electrically connected to at least one trace of the plurality of conductive traces 625 and at least one trace of the subset of conductive traces 630. In some embodiments, forming the flexible printed circuit board 600 further comprises forming at least one contact via 640 in the second polymer layer 635 of each of the plurality of end portions 620 such that the at least one contact via 645 is in electrical contact with at least one trace of the plurality of conductive traces 625 and at least one trace of the subset of conductive traces 630. The contact vias 645 can e.g. be formed with conductive material using conventional lithographic, etching, and cleaning processes, known to those of skill in the art. The contact vias 645 may be connected to the at least one trace of the subset of conductive traces 630 directly or indirectly by way of a wiring layer (e.g., a wiring layer formed in conjunction with deposition of the subset of conductive traces 630 in step 6C). In some embodiments, the conductive material is lined on at least a portion of the walls of the via hole. In other embodiments, the conductive material fills the via hole.

Figure 6J:
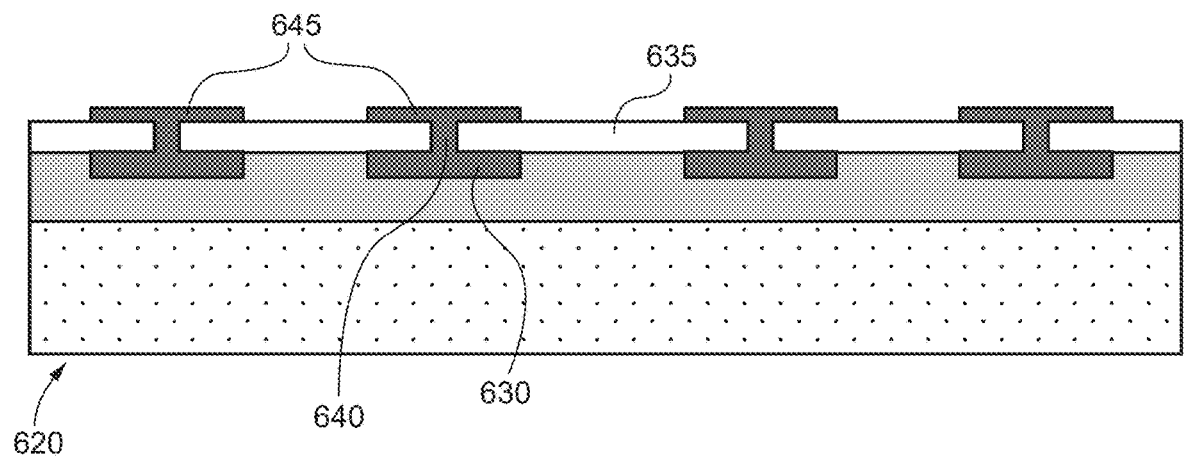
Figure 6K:
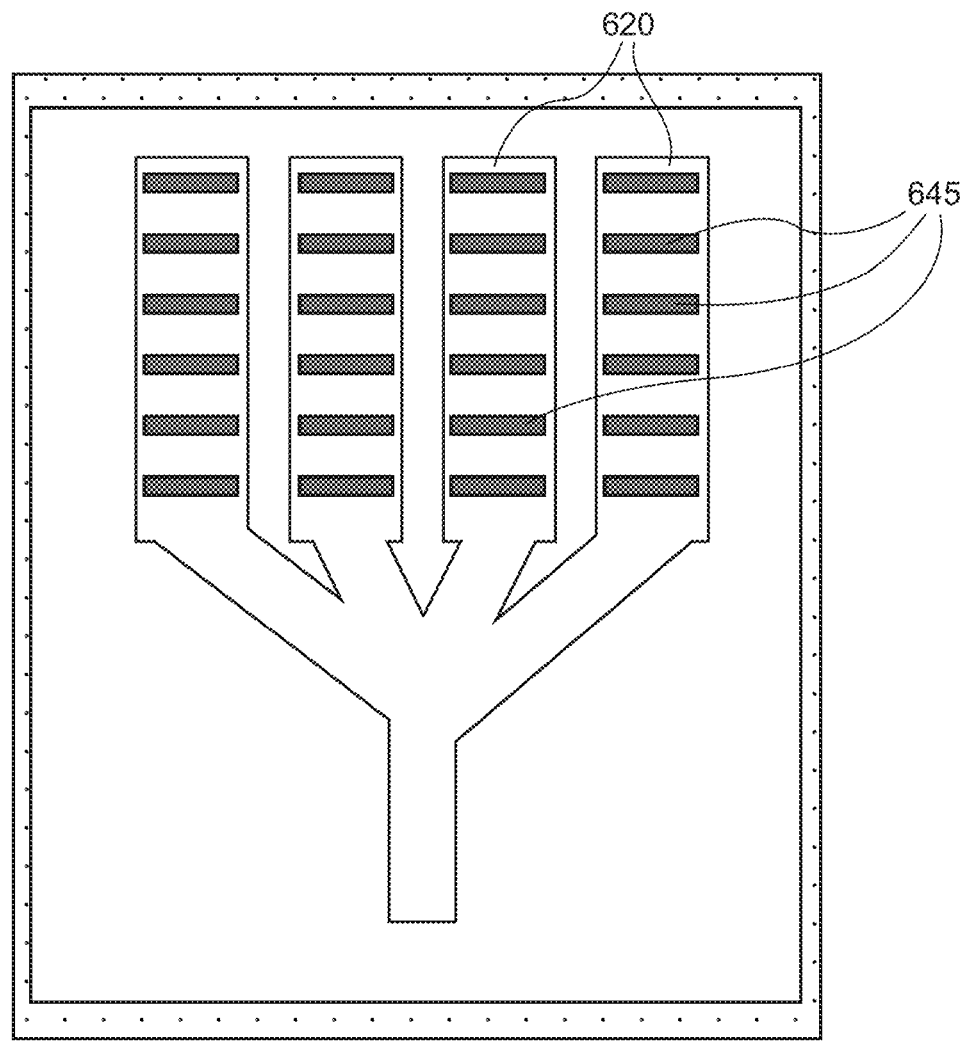

FIG. 6J shows forming at least one bond pad 645 on the second polymer layer 635 of each of the plurality of end portions 620 such that each bond pad 645 is in electrical contact with at least one contact via 640. In some embodiments, forming the bond bad 645 comprises forming a wiring layer 650 in a pattern on the second polymer layer 635. The wiring layer 650 may be formed in manner similar described with respect to the conductive traces 625 and the subset of conductive traces 630, and thus is not repeated here. FIG. 6K shows a top view of the bonds pads 645 formed on each of the plurality of end portions 620.

Figure 6L:
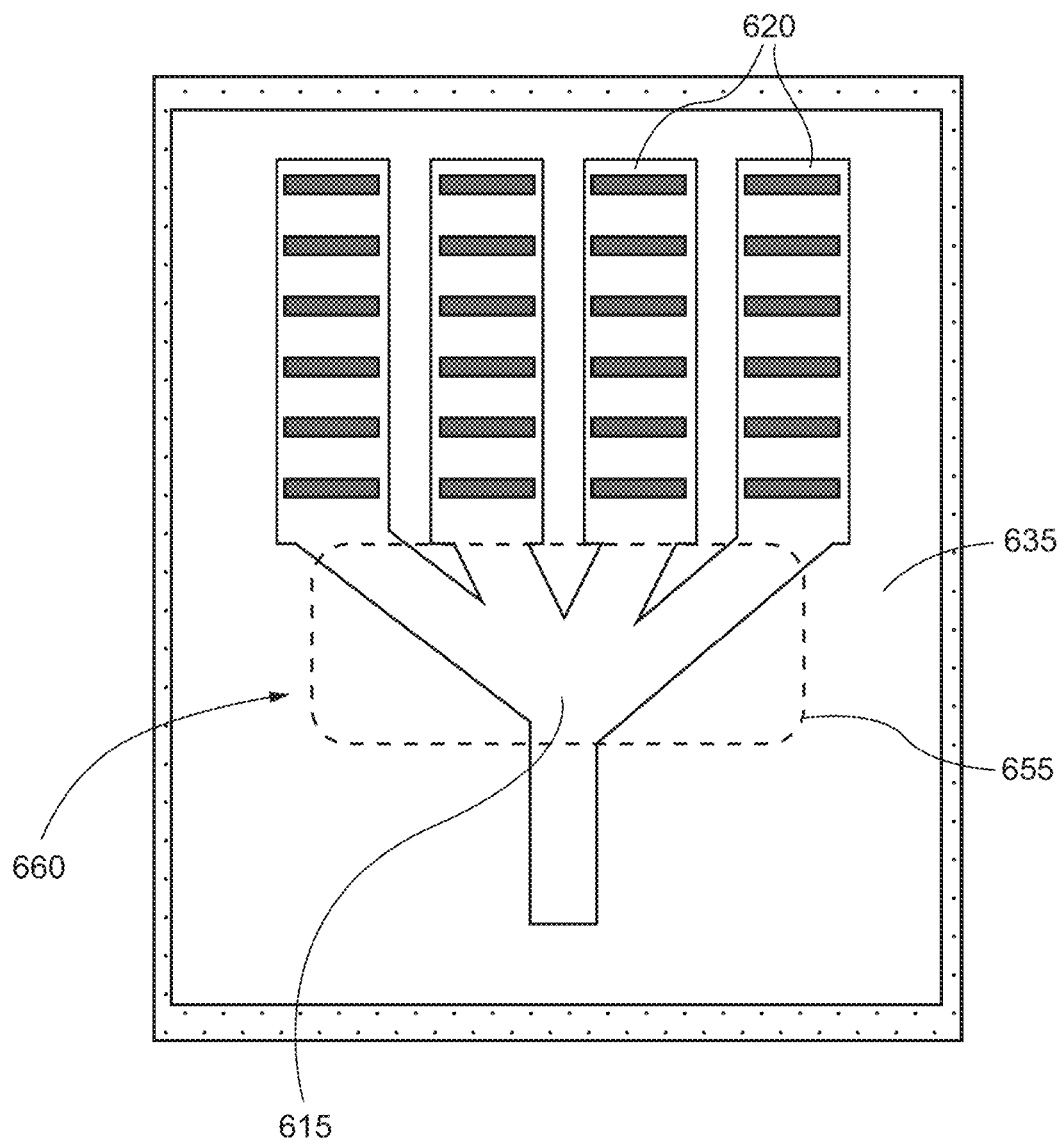

FIG. 6L shows an optional third polymer layer 655 formed over the second polymer layer 635 in a region 660 between the main body portion 615 and the plurality of end portions 620 in order to reinforce joints between each of the end portions 620 and the main body portion 615. The third polymer layer 655 may be comprised of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a thermoplastic or thermosetting polymer. For example, the polymer may be a polyimide, a LCP, silicone, parylene, a PEEK, or combinations thereof. The third polymer layer 655 may be comprised of the same material or a different material from that of the first polymer layer 605 and/or the second polymer layer 635.

Figure 6M:
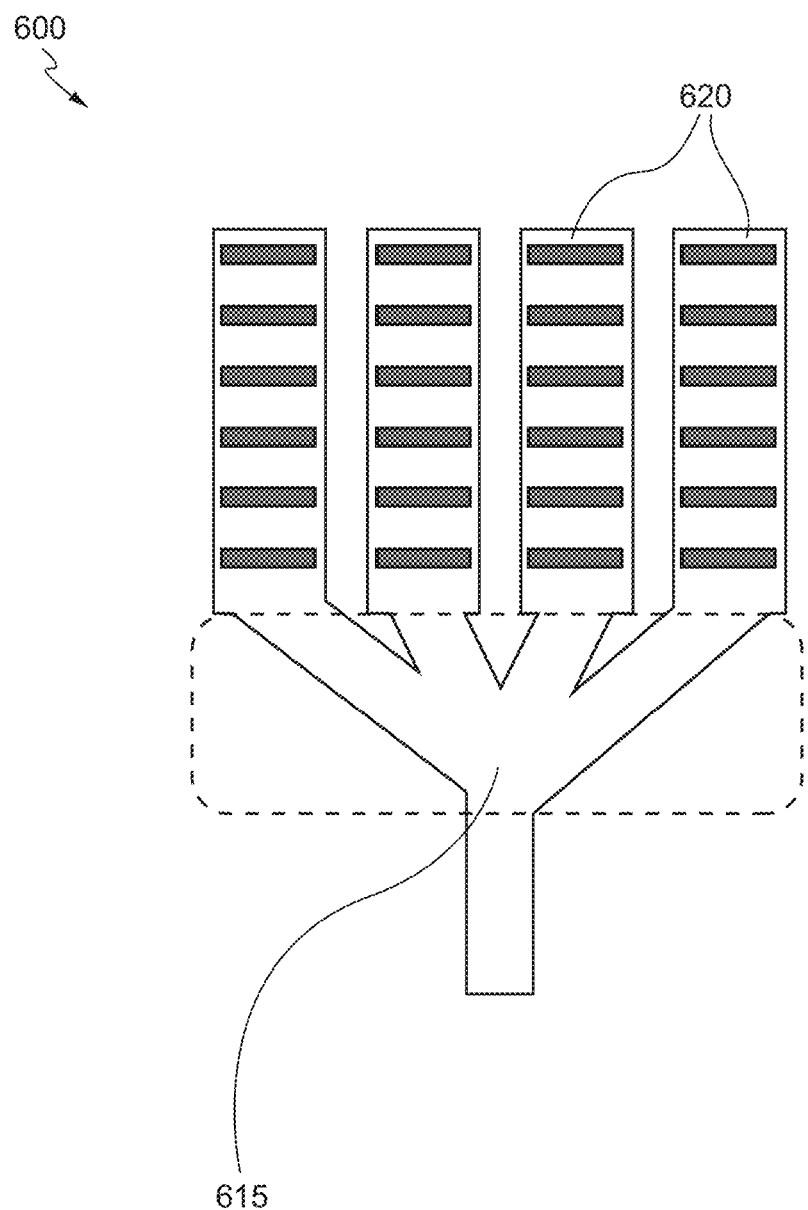

FIG. 6M shows a final monolithic structure of the flexible printed circuit board 600 including a main body portion 615 and a plurality of end portions 620. For example, the flexible printed circuit board 600 may be cut from the first polymer layer 605 and the second polymer layer 635, and comprises a main body portion 615 and a plurality of end portions 620 extending from the main body portion 605. In some embodiments, the cutting is accomplished using a laser and known techniques. Optionally, the flexible printed circuit board 600 may be detached from the substrate 610.

Figure 7A:
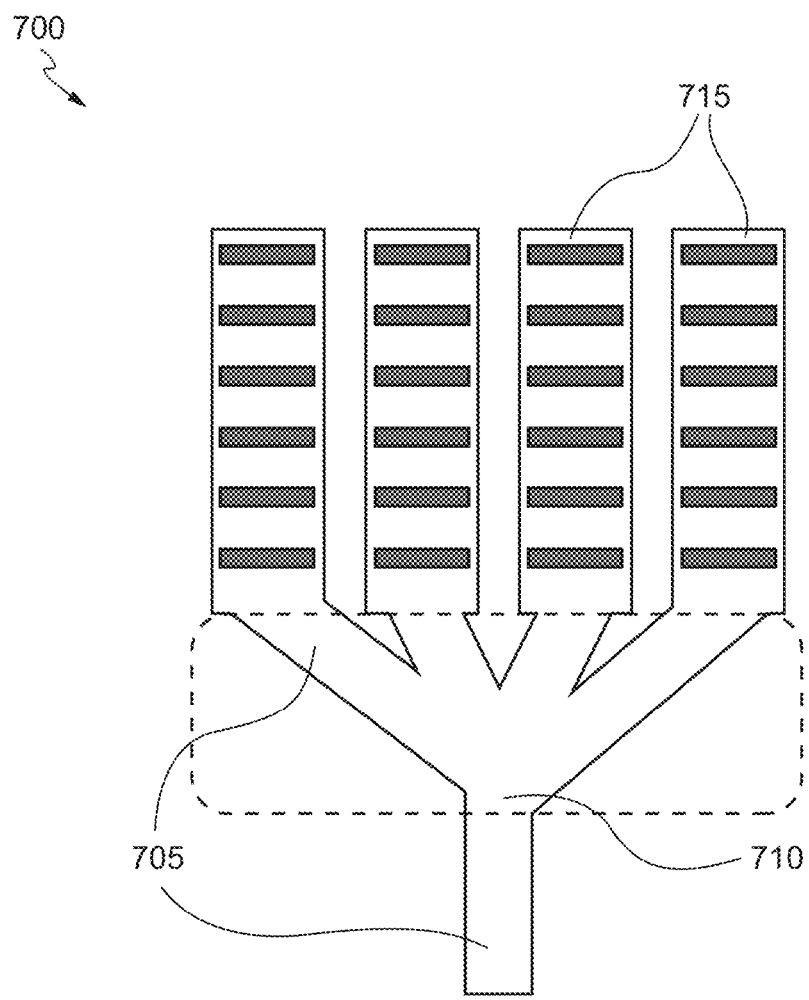
FIGS. 7A-7H show top views illustrating a method of fabricating a branched connector in accordance with various embodiments.

FIGS. 7A-7H show structures and respective processing steps for fabricating a thin-film branched connector 700 (e.g., a branched connector fabricated by injecting and curing a thermosetting polymer) in accordance with various aspects of the invention. FIG. 7A shows a beginning structure 705 for a branched connector including a main body portion 710 and a plurality of end portions 715 extending from the main body portion 710. The beginning structure 705 may be formed in accordance with the processes describe herein with reference to FIGS. 6A-6M. For example, the beginning structure 705 may be laser cut in a branched design from first and second polymer layers fabricated with electroplated traces and bond pads.

Figure 7B:
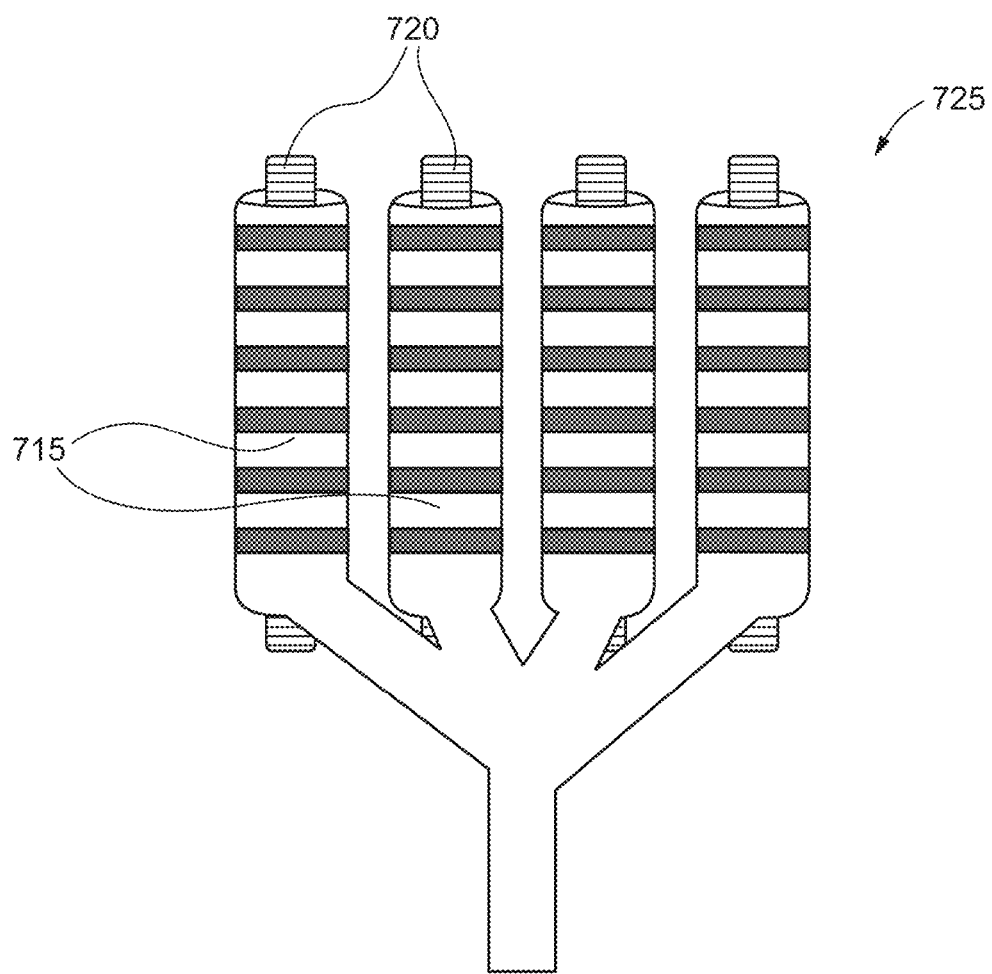

FIG. 7B shows each of the end portions 715 at least partially wrapped around a mandrel 720, respectively, such that each of the end portions 715 is in a shape of a cylindrical tube to form an intermediate structure 725. In various embodiments, the mandrels 720 are selected and the wrapping is controlled such that the cylindrical tubes comprise one or more characteristics including a radius, a split or gap, or non-overlapping ends. The radius is dictated by the outer diameter of the mandrels 720 and may be from 300 μm to 900 μm, from 500 μm to 800 μm, or from 6000 μm to 700 μm, for example, about 650 μm. In some embodiments, each of the end portions 715 is partially wrapped around a mandrel 720, respectively, such that the plurality of cylindrical end portions are a plurality of split cylindrical end portions, and each split cylindrical end portion of the plurality of split cylindrical end portions comprises a gap for the split having a predefined width. In some embodiments, the mandrels 725 comprise a coating such as polytetrafluoroethylene (PTFE) for easier removal of the end portions 715 from the mandrels 725.

Figure 7C:
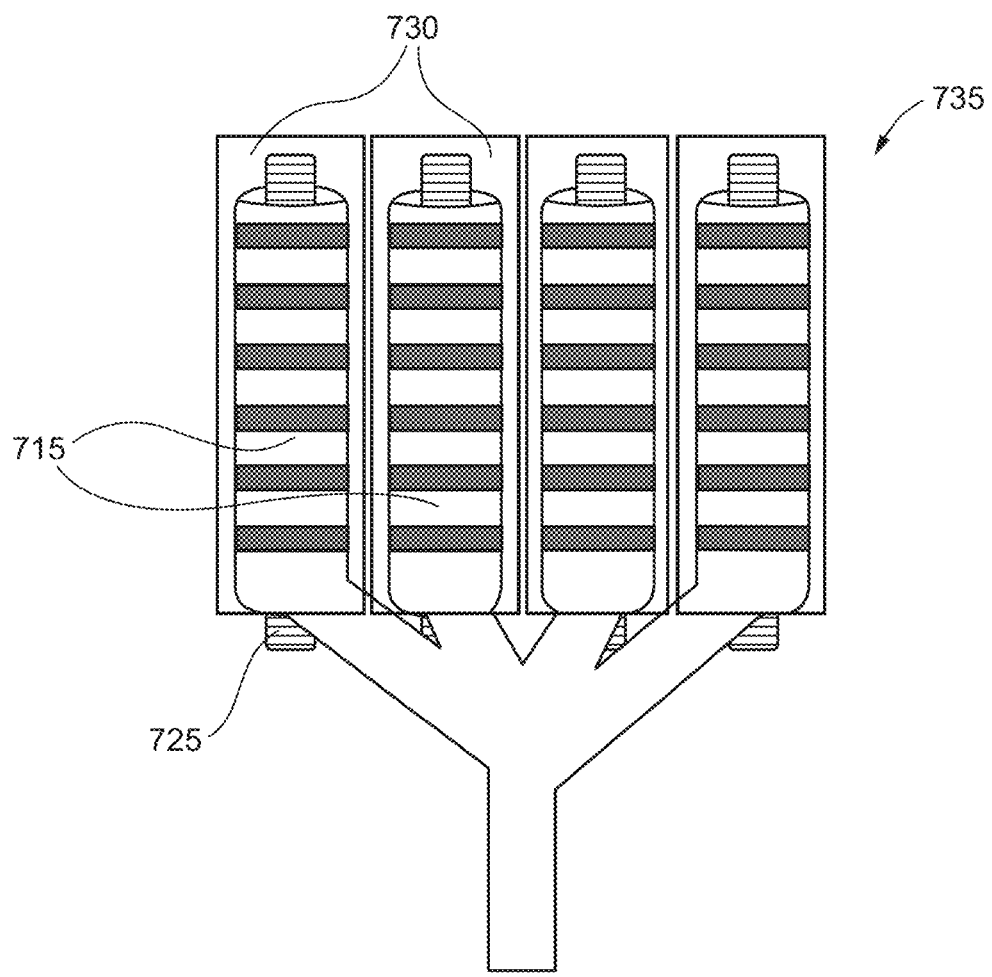
Figure 7D:
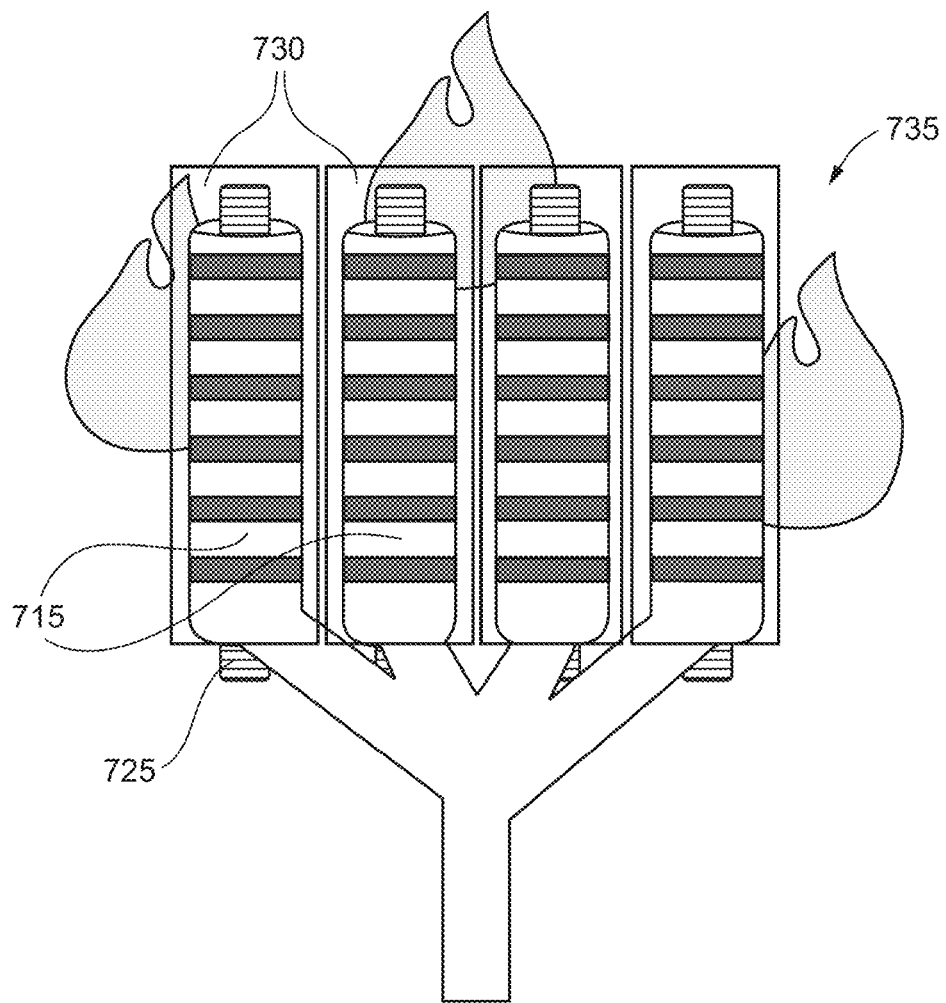
Figure 7E:
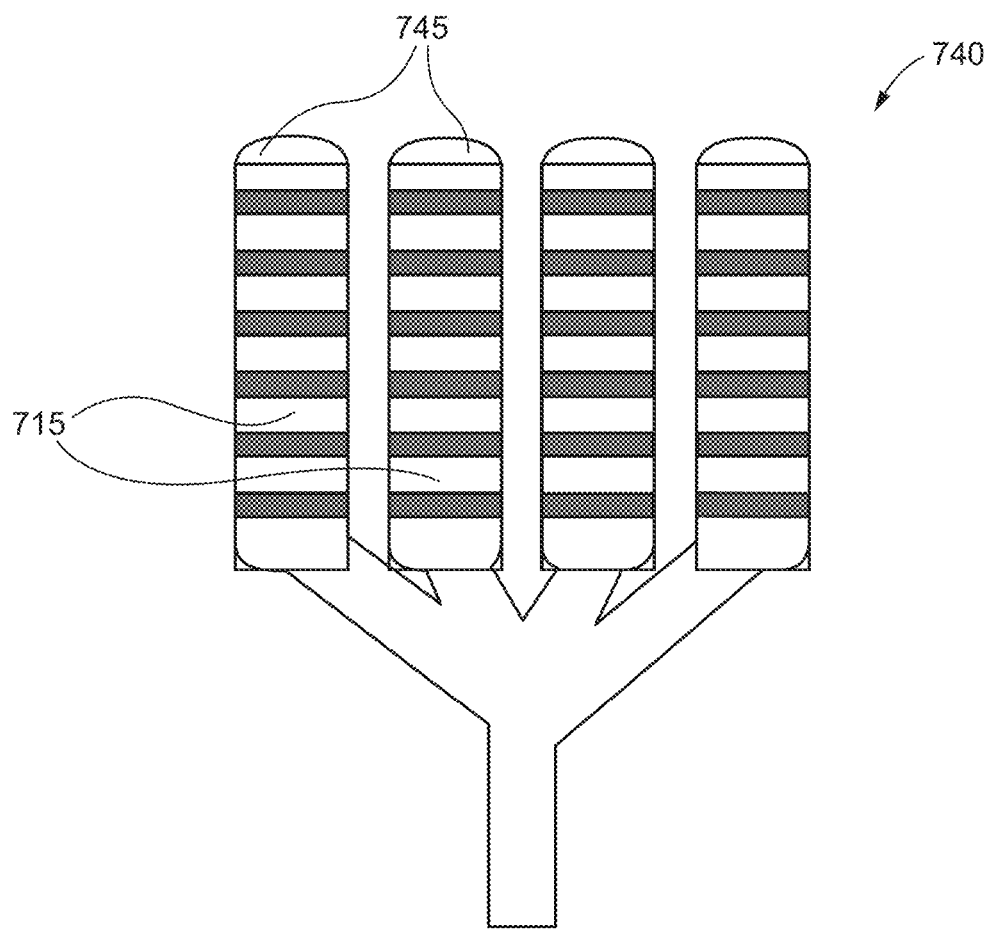

FIG. 7C shows the end portions 715 of the intermediate structure 725 being inserted into heat shrink tubes 730, respectively, to form an intermediate structure 735. In various embodiments, the heat shrink tubes 730 are comprised of one or more polymer resins, for example, a fluoropolymer such as the FluoroPEELZ® peelable heat shrink tubes, fluorinated ethylene propylene (FEP), etc. FIG. 7D shows intermediate structure 735 being heated to heat shrink the tubes 730 to define an outer diameter of the cylindrical tubes of the intermediate structure 735. The heating process may include baking the structure in an oven, use of a heat gun, application of hot air, like methods, or any combination thereof. In various embodiments, the intermediate structure 735 is heated at 170° C. to 210° C., for example about 190° C., for 15 to 40 minutes, for example 25 minutes. Thereafter, the intermediate structure 735 is cooled (e.g., at ambient temperature), and the mandrels 725 are withdrawn to obtain the intermediate structure 740, as shown in FIG. 7E. In various embodiments, the heating process results in each of the end portions 715 being in a shape of a cylindrical tube with a lumen 745.

Figure 7F:
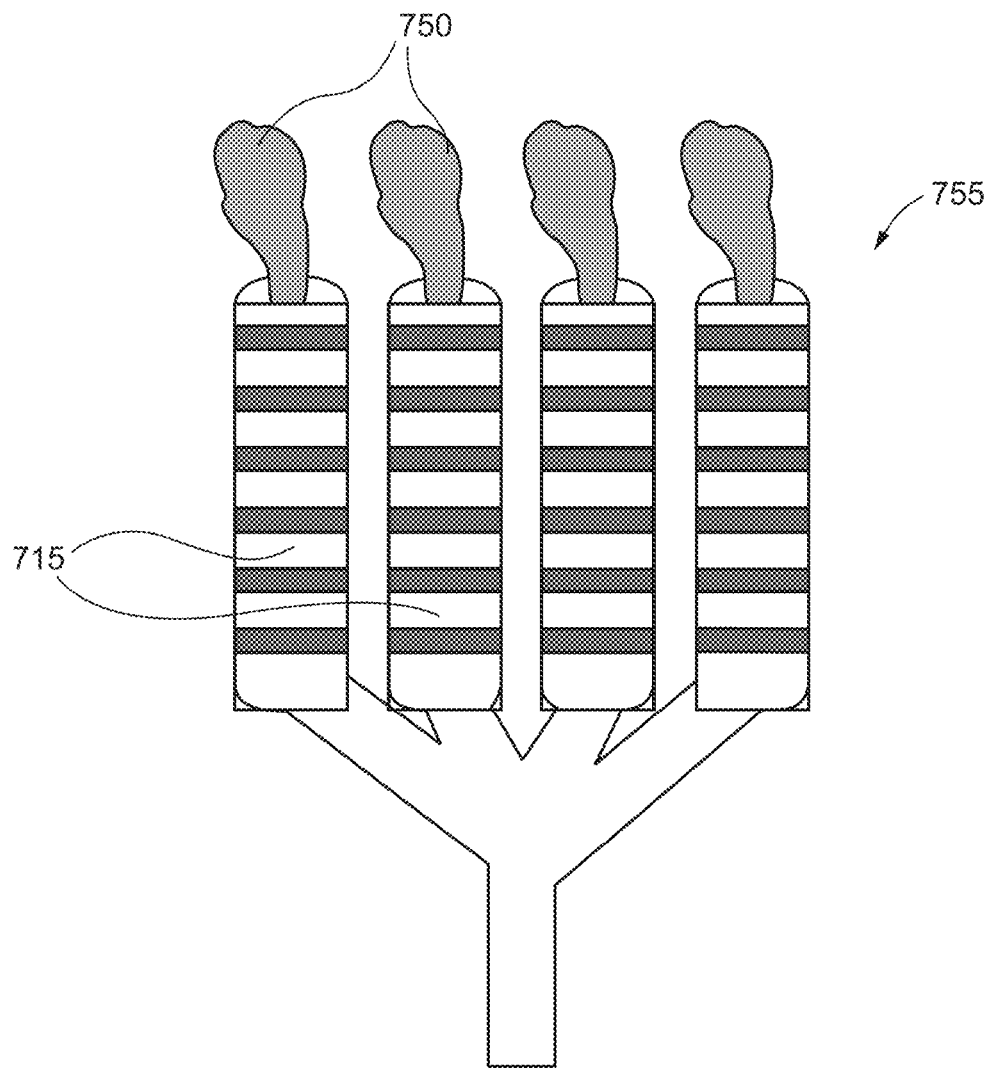

FIG. 7F shows a polymer 750 being injected into each of the end portions 715 of the intermediate structure 740. In various embodiments, the polymer is comprised of a medical grade polymer material, for example, a polymer such as epoxy, a polyurethane, a copolymer thereof, or a blend thereof. In some embodiments, the polymer is a thermosetting polymer. In certain embodiments, the polymer is comprised of a medical grade polymer material with a Shore durometer measured on a Shore 00 Scale of greater than 70D when cured. (Shore durometer is defined as a material's resistance to indentation). The polymer 750 may be injected into each of the end portions 715 one or more times in order to completely fill the length of the cylindrical tubes or a portion of the length of the cylindrical tubes to obtain the intermediate structure 755.

Figure 7G:
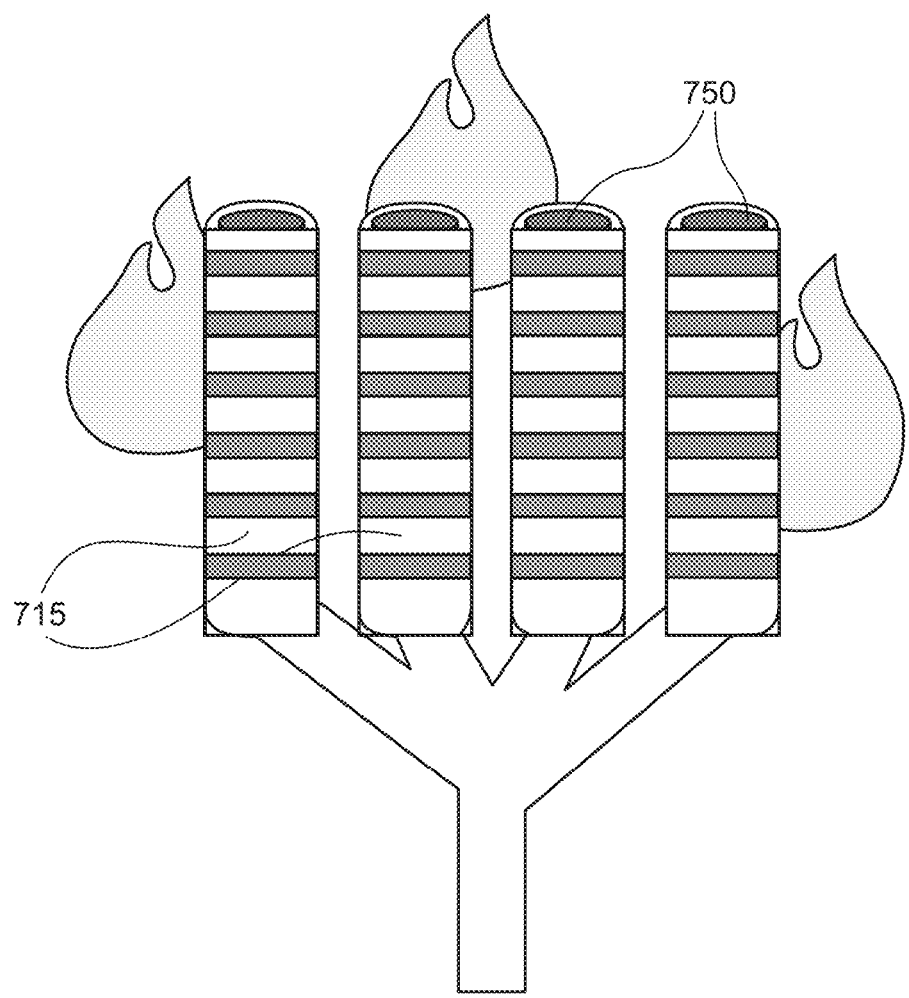
Figure 7H:
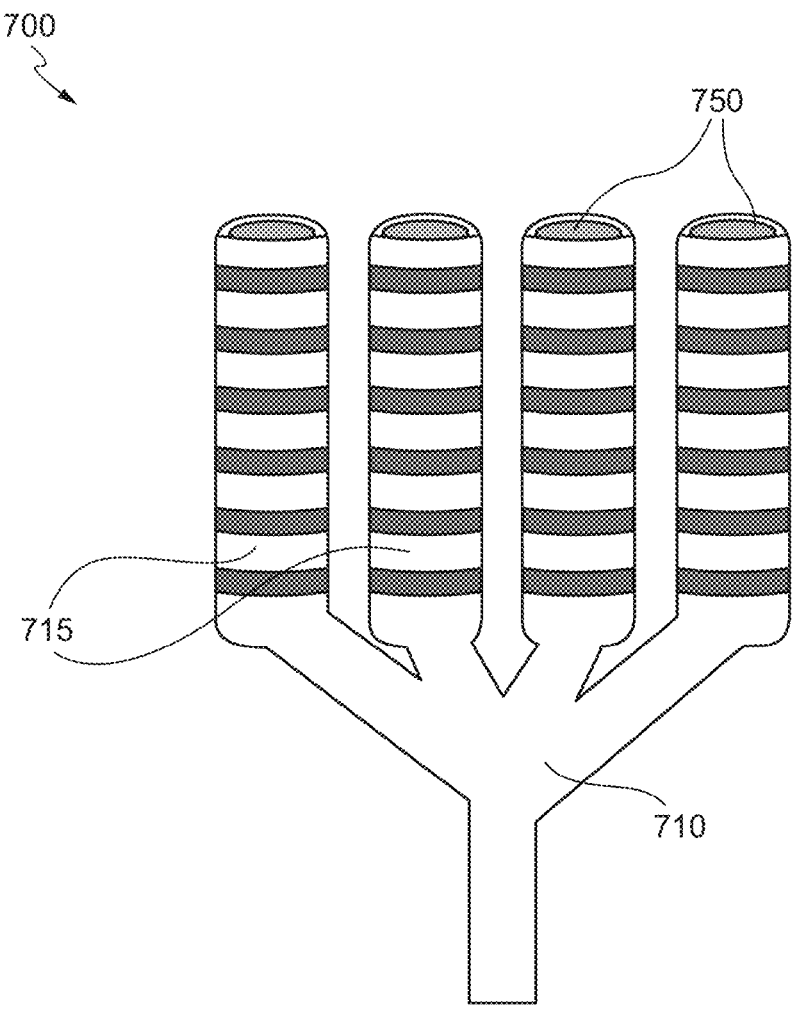

FIG. 7G shows intermediate structure 755 being heated to thermally cure (e.g., thermoset) the polymer 750. The heating process may include heating the structure in an oven, use of a heat gun, application of hot air, like methods, or any combination thereof. In various embodiments, the intermediate structure 755 is heated at 80° C. to 115° C., for example about 100° C., for 5 to 20 minutes, for example 10 minutes. Thereafter, the intermediate structure 755 is cooled (e.g., at ambient temperature) and the heat shrink tubes 730 are peeled away to obtain the final structure of the thin-film branched connector 700 shown in FIG. 7H. The final structure comprises each of the end portions 715 having the first and second polymer layers at least partially wrapped around a core made of the polymer 750. In some embodiments, the injection and heating processes result in at least a portion of each of the end portions 715 embedding into the polymer 750, respectively. In some embodiments, the injection and heating processes embeds a portion of each of the end portions 715 into the polymer 750, respectively, forming conjoined solid tubes without a lumen.

Figure 8A:
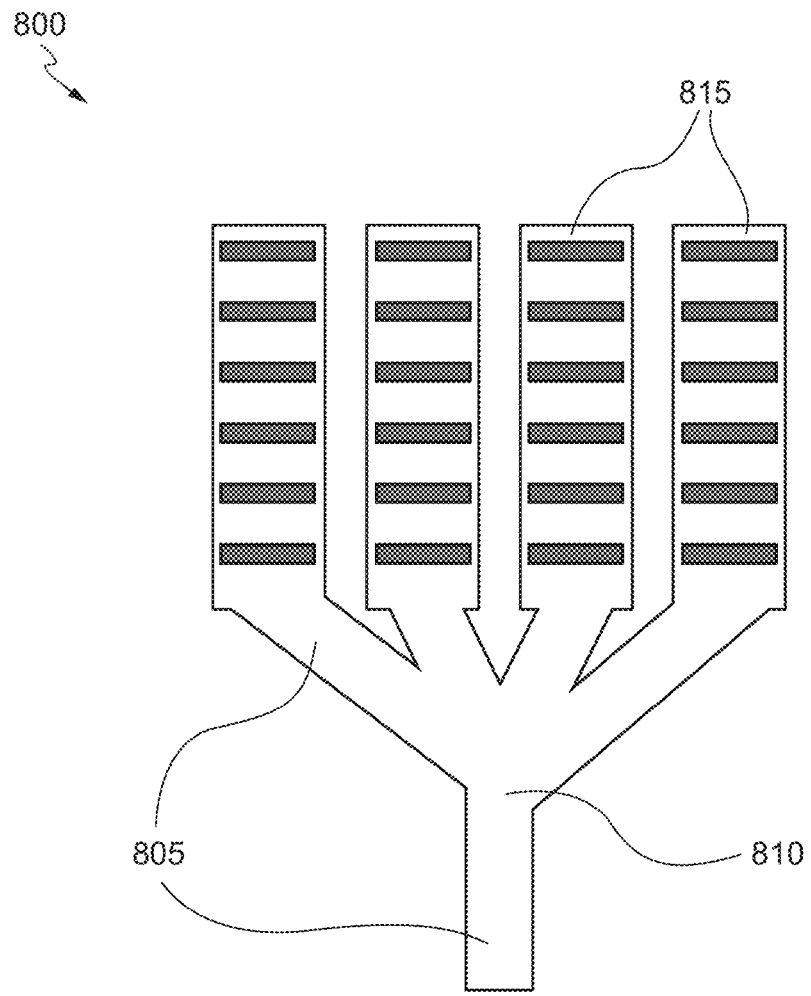
FIGS. 8A-8E show top views illustrating an alternative method of fabricating a branched connector in accordance with various embodiments.

FIGS. 8A-8E show structures and respective processing steps for fabricating an alternative thin-film branched connector 800 (e.g., a branched connector fabricated by reflowing a predefined thermoplastic polymer core) in accordance with various aspects of the invention. FIG. 8A shows a beginning structure 805 for a branched connector including a main body portion 810 and a plurality of end portions 815 extending from the main body portion 810. The beginning structure 805 may be formed in accordance with the processes describe herein with reference to FIGS. 6A-6M. For example, the beginning structure 805 may be laser cut in a branched design from first and second polymer layers fabricated with electroplated traces and bond pads.

Figure 8B:
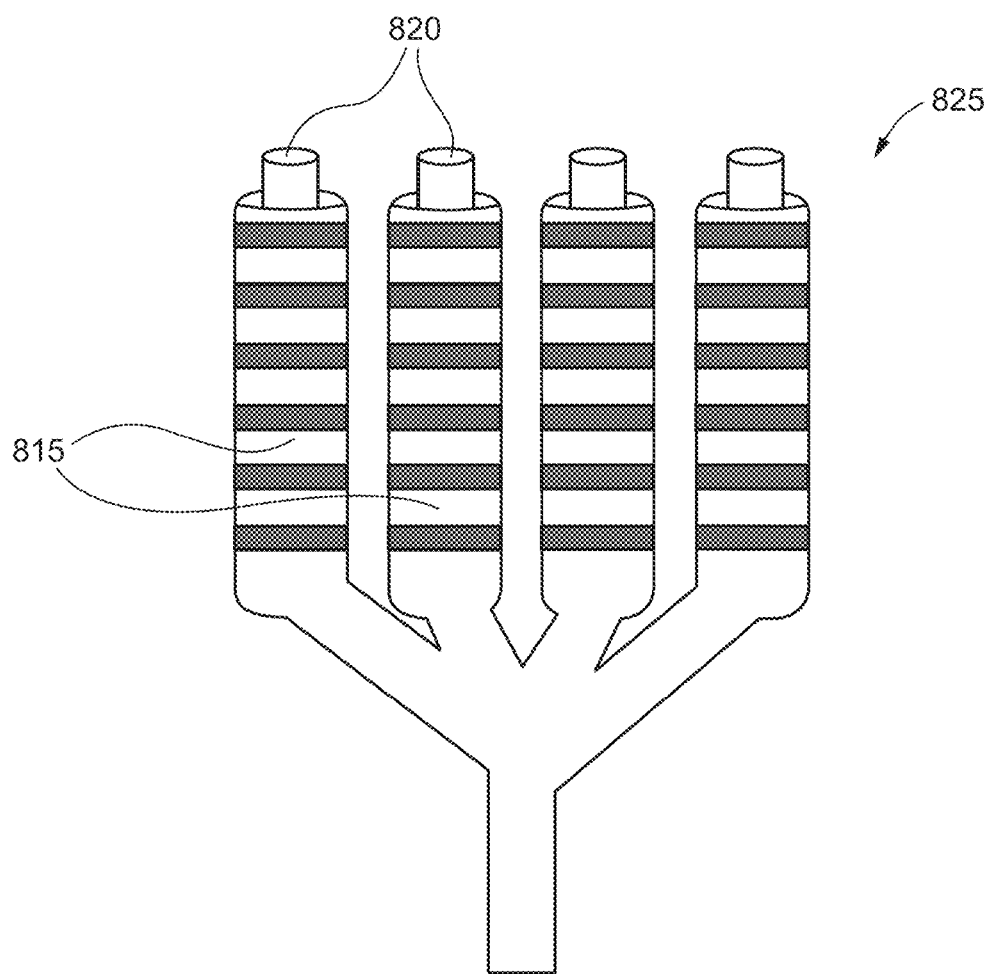

FIG. 8B shows each of the end portions 815 at least partially wrapped around a polymer tube 820, respectively, such that each of the end portions 815 is in a shape of a cylindrical tube to form an intermediate structure 825. In various embodiments, the polymer tubes 820 are selected and the wrapping is controlled such that the cylindrical tubes comprise one or more characteristics including a radius, a split or gap, or non-overlapping ends. The radius is dictated by the outer diameter of the polymer tubes 820 and may be from 50 µm to 700 µm, from 100 µm to 600 µm, or from 100 µm to 450 µm, for example, about 350 µm. In some embodiments, each of the end portions 815 is partially wrapped around a polymer tube 820, respectively, such that the plurality of cylindrical end portions are a plurality of split cylindrical end portions, and each split cylindrical end portion of the plurality of split cylindrical end portions comprises a gap for the split having a predefined width. In some embodiments, the polymer tubes 820 comprise a thermoplastic polymer. In certain embodiments, the thermoplastic polymer is polyurethane.

Figure 8C:
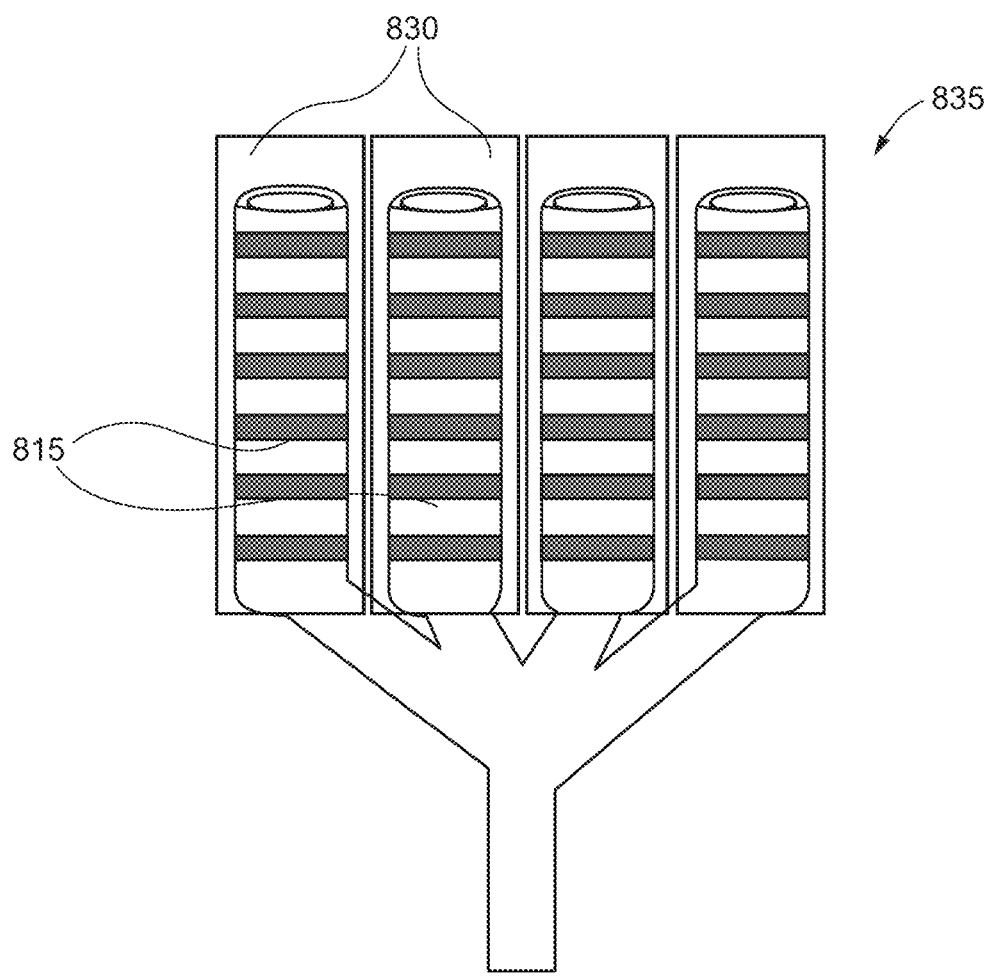
Figure 8D:
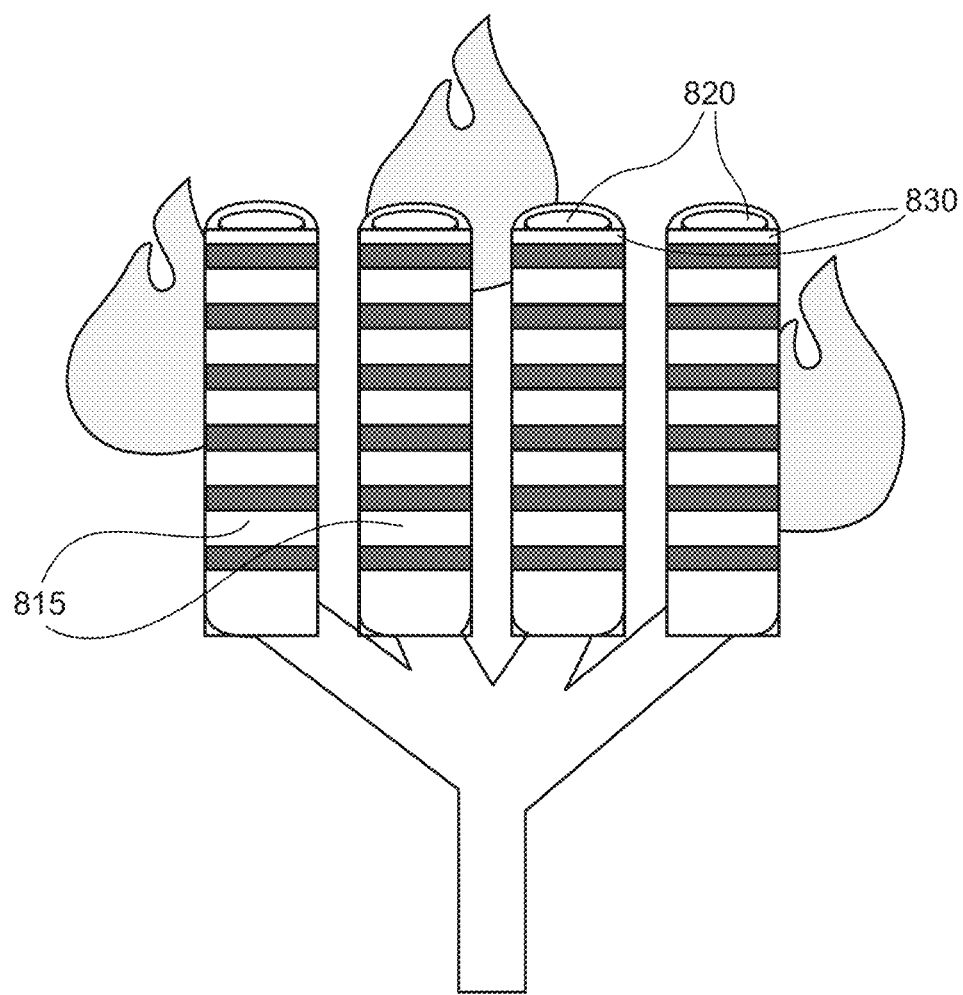
Figure 8E:
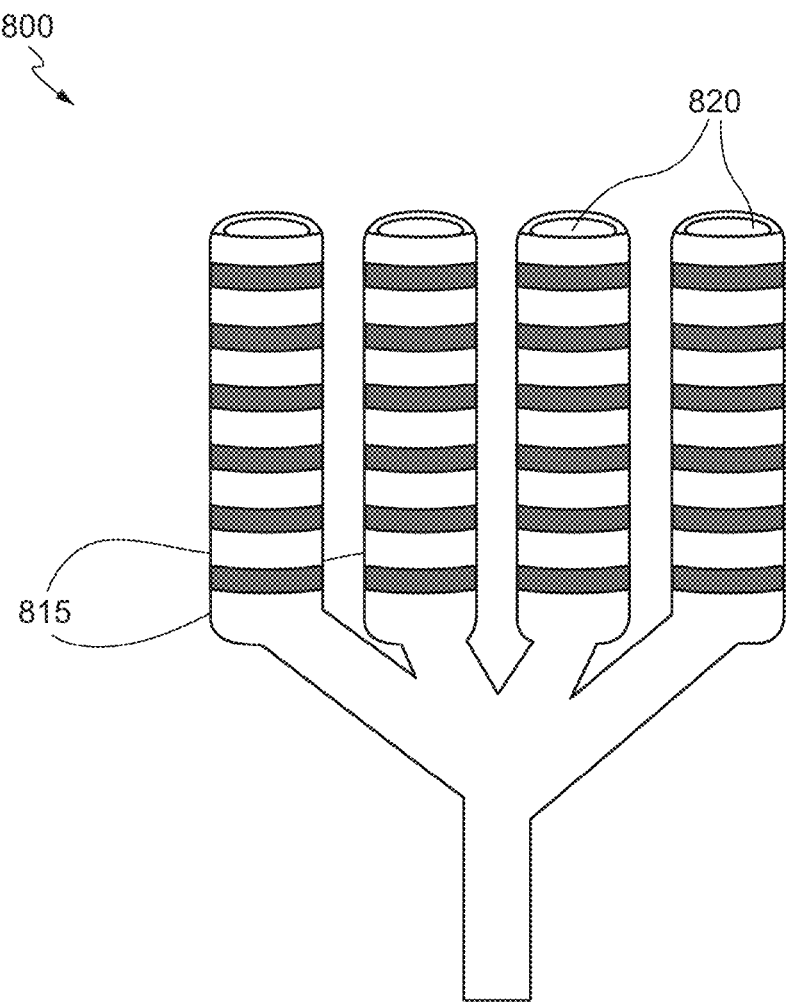

FIG. 8C shows the end portions 815 of the intermediate structure 825 being inserted into heat shrink tubes 830, respectively, to form an intermediate structure 835. In various embodiments, the heat shrink tubes 830 are comprised of one or more polymer resins, for example, a fluoropolymer such as the FluoroPEELZ® peelable heat shrink tubes, fluorinated ethylene propylene (FEP), etc. FIG. 8D shows intermediate structure 835 being heated to heat shrink the tubes 830 to define an outer diameter of the cylindrical tubes of the intermediate structure 835, and at the same time melt and reflow the polymer tubes 820 to embed each of the end portions 815 in the polymer tubes 820, respectively. The heating process may include baking the structure in an oven, use of a heat gun, application of hot air, like methods, or any combination thereof. In various embodiments, the intermediate structure 835 is heated at 170° C. to 210° C., for example about 190° C., for 15 to 40 minutes, for example 25 minutes. Thereafter, the intermediate structure 835 is cooled (e.g., at ambient temperature), the heat shrink tubes 830 are peeled away to obtain the final structure of the thin-film branched connector 800 shown in FIG. 8E. The final structure comprises each of the end portions 815 having the first and second polymer layers at least partially wrapped around a core made of the polymer tube 820. In some embodiments, the heating processes result in at least a portion of each of the end portions 815 embedding into the polymer tubes 820, respectively. In some embodiments, the heating processes embed a portion of each of the end portions 815 into the polymer tubes 820, respectively, forming conjoined solid tubes without a lumen.

While the manufacturing processes of branched connectors have been described at some length and with some particularity with respect to a specific steps, it is not intended that the processes be limited to any such particular set of steps. Instead, it should be understood the manufacturing processes described herein are exemplary embodiments, and that the manufacturing processes are to be construed with the broadest sense to include variations of the steps to meet specific design and/or performance need described herein, as well as other variations that are well known to those of skill in the art. For example, the various intermediate and final structures described may be adjusted or modified with treatments to increase wettability of the thin-film lead assembly or to seal the ends of the lumens to meet specific design and/or performance needs. Furthermore, it is to be understood that other steps have been omitted from the description of the manufacturing processes for simplicity and clarity. The omitted steps may include obtaining or fabricating the polymer tubes, obtaining or fabricating the heat shrink tubes, waiting predetermined amounts of time for curing or thermosetting, etc.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A thin-film lead assembly comprising:
   a cable comprising a proximal end, a distal end, a first supporting structure that extends from the proximal end to the distal end, and a plurality of conductive traces formed on a portion of the first supporting structure;
   an electrode assembly formed on the first supporting structure at the distal end of the cable, wherein the electrode assembly comprises one or more electrodes in electrical connection with one or more conductive traces of the plurality of conductive traces; and
   a branched connector comprising: (i) a main body comprising a second supporting structure and a plurality of conductive connector traces, and (ii) a plurality of plugs extending from the main body, each plug of the plurality of plugs comprises the second supporting structure and a subset of conductive connecting traces from the plurality of conductive connecting traces,
   wherein each trace from the subset of conductive connecting traces terminates at a bond pad exposed on a surface of the second supporting structure, and
   wherein the plurality of conductive connector traces of the branched connector are in electrical contact with the plurality of conductive traces of the cable, respectively.

2. The thin-film lead assembly of claim 1, wherein the second supporting structure is comprised of one or more layers of dielectric material, and the dielectric material is polyimide, liquid crystal polymer, parylene, polyether ether ketone, or a combination thereof.

3. The thin-film lead assembly of claim 1, wherein the plurality of conductive connector traces are comprised of one or more layers of conductive material, and the conductive material is platinum (Pt), platinum/iridium (Pt/Ir), titanium (Ti), gold/titanium (Au/Ti), or any alloy thereof.

4. The thin-film lead assembly of claim 1, wherein the second supporting structure of each plug is planar.

5. The thin-film lead assembly of claim 1, wherein the second supporting structure of each plug is a cylindrical tube.

6. The thin-film lead assembly of claim 5, wherein the second supporting structure of each of the plugs comprises a first layer of dielectric material and a second layer of dielectric material with the subset of conductive connecting traces buried between the first layer of dielectric material and the second layer of dielectric material.

7. The thin-film lead assembly of claim 6, wherein each bond pad is a split annular ring positioned around an axis of the cylindrical tube and exposed on the surface of the cylindrical tube.

8. The thin-film lead assembly of claim 7, wherein each split annular ring is spaced apart from one another on the surface of the cylindrical tube by a region of the first layer of the dielectric material.

9. The thin-film lead assembly of claim 7, wherein the cylindrical tube comprises: (i) a plurality of layers of dielectric material comprising the first layer of dielectric material that defines an outer diameter of the cylindrical tube and the second layer of dielectric material that defines an inner diameter of the cylindrical tube; and (ii) a core that at least partially fills an interior of the cylindrical tube defined by the inner diameter of the cylindrical tube.

10. The thin-film lead assembly of claim 9, wherein the plurality of layers of dielectric material are at least partially wrapped around the core.

11. The thin-film lead assembly of claim 10, wherein the plurality of layers of dielectric material are formed as a split cylindrical tube wrapped around the core, and the split cylindrical tube comprises a gap for a split having a predefined width.

12. The thin-film lead assembly of claim 11, wherein the first layer of dielectric material comprises at least one via for each bond pad, and the at least one via for each bond pad comprises a conductive material for electrically connecting each bond pad to at least one trace of the subset of conductive connecting traces such that each trace from the subset of conductive connecting traces terminates at a bond pad.

13. The thin-film lead assembly of claim 12, wherein the first layer of dielectric material is a high temperature liquid crystal polymer, and the second layer of dielectric material is a low temperature liquid crystal polymer.

14. The thin-film lead assembly of claim 13, wherein the core is comprised of one or more layers of material such that the core has a Shore durometer of greater than 70D.

15. A neuromodulation system comprising:
a neurostimulator comprising an electronics module;
a cable comprising a supporting structure and a plurality of conductive traces formed on a portion of the supporting structure, wherein the supporting structure is comprised of one or more layers of dielectric material;
an electrode assembly formed on the supporting structure, wherein the electrode assembly comprises one or more electrodes in electrical connection with one or more conductive traces of the plurality of conductive traces; and
a branched connector formed on the supporting structure at a proximal end of the cable, wherein the branched connector comprises: (i) a main body comprising the supporting structure and the plurality of conductive traces, and (ii) a plurality of plugs extending from the main body, each plug of the plurality of plugs comprises the supporting structure and a subset of conductive traces from the plurality of conductive traces,
wherein the branched connector electrically connects each subset of conductive traces from the plurality of conductive traces to the electronics module.

16. The neuromodulation system of claim 15, wherein each trace from the subset of conductive traces terminates at a bond pad exposed on a surface of the supporting structure.

17. The neuromodulation system of claim 15, wherein the supporting structure of each plug is planar.

18. The neuromodulation system of claim 15, wherein the supporting structure of each plug is a cylindrical tube.

19. The neuromodulation system of claim 18, wherein the supporting structure of each of the plugs comprises a first layer of dielectric material and a second layer of dielectric material with the subset of conductive traces buried between the first layer of dielectric material and the second layer of dielectric material.

20. The neuromodulation system of claim 19, wherein each bond pad is a split annular ring positioned around an axis of the cylindrical tube and exposed on a surface of the cylindrical tube.

* * * * *